(12) United States Patent
Li et al.

(10) Patent No.: US 9,334,533 B2
(45) Date of Patent: *May 10, 2016

(54) METHOD FOR DETECTING VARIATIONS IN NUCLEIC ACID SEQUENCES

(71) Applicant: XIAMEN UNIVERSITY, Xiamen (CN)

(72) Inventors: Qingge Li, Xiamen (CN); Qiuying Huang, Xiamen (CN)

(73) Assignee: XIAMEN UNIVERSITY, Xiamen (CN)

( * ) Notice: Subject to any disclaimer, the term of this patent is extended or adjusted under 35 U.S.C. 154(b) by 133 days.

This patent is subject to a terminal disclaimer.

(21) Appl. No.: 14/182,067

(22) Filed: Feb. 17, 2014

(65) Prior Publication Data

US 2014/0162898 A1    Jun. 12, 2014

Related U.S. Application Data

(63) Continuation of application No. 13/322,716, filed as application No. PCT/CN2010/000753 on May 26, 2010, now Pat. No. 8,691,504.

(30) Foreign Application Priority Data

May 26, 2009  (CN) .......................... 2009 1 0143480

(51) Int. Cl.
*C12Q 1/68* (2006.01)
*C07H 21/00* (2006.01)
(52) U.S. Cl.
CPC ............ *C12Q 1/6858* (2013.01); *C12Q 1/6827* (2013.01)
(58) Field of Classification Search
CPC ......... C12Q 1/68; C12Q 1/6827; C07H 21/00
See application file for complete search history.

(56) References Cited

U.S. PATENT DOCUMENTS

| | | | |
|---|---|---|---|
| 6,958,390 B1 | 10/2005 | WalkerPeach et al. | |
| 7,476,733 B2 | 1/2009 | Carvalho et al. | |
| 7,541,448 B2 | 6/2009 | Heindl et al. | |
| 7,718,361 B2 | 5/2010 | Baron et al. | |
| 8,288,522 B2 | 10/2012 | Luo et al. | |
| 8,691,504 B2 * | 4/2014 | Li .......................... | C12Q 1/6827 435/6.1 |
| 2003/0148280 A1 | 8/2003 | Harris et al. | |
| 2003/0215826 A1 | 11/2003 | Mayrand | |
| 2005/0112637 A1 | 5/2005 | Chatterjee | |
| 2006/0216708 A1 | 9/2006 | Venema | |
| 2007/0178485 A1 | 8/2007 | El-Deiry et al. | |
| 2007/0196852 A1 | 8/2007 | Heindl et al. | |
| 2007/0231809 A1 | 10/2007 | Chou et al. | |
| 2008/0026386 A1 | 1/2008 | Behrens et al. | |
| 2010/0285535 A1 | 11/2010 | Ankenbauer et al. | |
| 2011/0136105 A1 | 6/2011 | Jantsch et al. | |
| 2012/0184017 A1 | 7/2012 | Chatterjee | |
| 2012/0237451 A1 | 9/2012 | Chen et al. | |
| 2013/0084343 A1 | 4/2013 | Vilanova et al. | |
| 2013/0102488 A1 | 4/2013 | Barrie et al. | |
| 2013/0157886 A1 | 6/2013 | Michot et al. | |

FOREIGN PATENT DOCUMENTS

| | | |
|---|---|---|
| CN | 1900312 A | 1/2007 |
| WO | 00/46398 A1 | 8/2000 |
| WO | 2008/109823 A2 | 9/2008 |

OTHER PUBLICATIONS

Barnes, The fidelity of Taq polymerase catalyzing PCR is improved by an N-terminal deletion, Gene 112 :29 (1992).
Bernard et al. Technical Advance : Homogeneous Multiplex Genotyping of Hemochromatosis Mutations with Fluorescent Hybridization Probes. American Journal of Pathology 153 (4) : 1055 (1998).
Bertina et al., Mutation in blood coagulation factor V associated with resistance to activated protein C.Nature 369 :64 (1994).
El-Hajj et al., "Use of Sloppy Molecular Beacon Probes for Identification of Mycobacterial Species," Journal of Clinical Microbiology, Vol. 47, No. 4, Apr. 2009, pp. 1190-1198.
Eom et al., Structure of Taq polymerase with DNA at the polymerase active site. Nature 382 :278 (1996).
Horejsh et al., A molecular beacon, bead-based assay for the detection of nucleic acids by flow cytometry.Nucleic Acids Research 33(2) :e13 (2005).
Huang et al., "Multiplex Fluorescence Melting Curve Analysis for Mutation Detection with Dual-Labeled, Self-Quenched Probes," PloS One, Apr. 2011, vol. 6, No. 4, pp. 1-9.
Huang, "Study on Real-Time PCR-Based Approaches for Multiple Targets Detection," Chinese Master's Theses Full-text Database, Basic Sciences, No. 12, Dec. 15, 2009, pp. 1-132 (in Chinese and English).
International Search Report for PCT/CN10/000753 mailed Sep. 2, 2010.
Kuhn et al., Hybridization of DNA and PNA molecular beacons to single-stranded and double-stranded DNA targets. JACS124(6) : 1097 (2002).
Lawyer et al., High-level expression, purification, and enzymatic characterization of full-length Thermus aquaticus DNA; polymerase and a truncated form deficient in 5' to 3' exonuclease activity. PCR Methods and Applications 2:275 (1993).
Lukhtanov et al., "Novel DNA probes with low background and high hybridization-triggered fluorescence," Nucleic Acids Research, 2007, vol. 35, No. 5, pp. 1-14.
Lyon, Mutation detection using fluorescent hybridization probes and melting curve analysis. Expert Reviews in Molecular Diagnosis 1 (1) : 92 (2001 ).
Mamotte, "Genotyping of Single Nucleotide Substitutions," Clinical Biochem Rev, vol. 27, Feb. 2006, pp. 63-75.

(Continued)

*Primary Examiner* — Ethan Whisenant
(74) *Attorney, Agent, or Firm* — Banner & Witcoff, Ltd.

(57) ABSTRACT

The present invention relates to a method and a kit for detecting nucleic acid sequence variation using melting curve analysis, especially relates to a method and a kit for detecting nucleic acid sequence variation by melting curve analysis using self-quenched probe. Said method provides the characteristics of the self-quenched probe employed, as well as the corresponding nucleic acid amplification conditions, so that the probe can bind to the amplified target sequence, and variations of the target sequence can be detected by melting curve analysis. The present invention also encompasses a kit assembled according to the method described.

27 Claims, 5 Drawing Sheets

(56) References Cited

OTHER PUBLICATIONS

Figure 1:
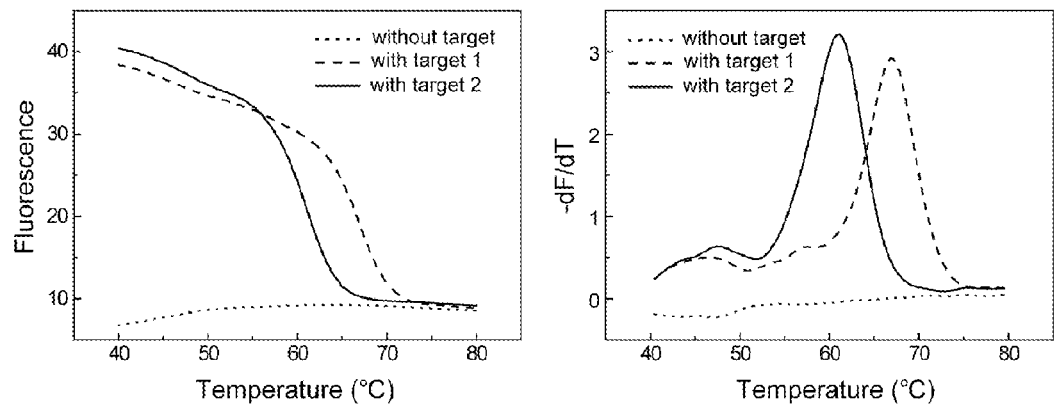

Marras et al., Multiplex detection of single-nucleotide variations using molecular beacons.; Genetic Analysis : Biomolecular Engineering 14 : 151 (1999).

Montgomery et al., "Simultaneous mutation scanning and genotyping by high-resolution DNA melting analysis," Nature Protocols, vol. 2, No. 1, 2007, pp. 59-66.

Petersen et al., "Short PNA molecular beacons for real-time PCR allelic discrimination of single nucleotide polymorphisms," Molecular and Cellular Probes, 2004, vol. 18, pp. 117-122.

Phillips et al.,Simultaneous detection of C282Y and H63D hemochromatosis mutations by dual-color probes. Molecular Diagnosis 5(2) : 107 (2000).

Pierce et al., "Detection of cystic fibrosis alleles from single cells using molecular beacons and a novel method of asymmetric real-time PCR," Molecular Human Reproduction, 2003, vol. 9, No. 12, pp. 815-820.

Saito et al., "Design of an efficient self-quenched molecular beacon for SNPs genotyping," Nucleic Acids Symposium Series, vol. 52, Sep. 8, 2008, pp. 359-360.

Tyagi et al., "Multicolor molecular beacons for allele discrimination," Nature Biotechnology, vol. 16, Jan. 1998, pp. 49-53.

Wang et al., Locked Nucleic Acid Molecular Beacons, JACS 127 : 15,664 (2005).

Wittwer et al., "Real-Time Multiplex PCR Assays," Methods, 2001, vol. 25, pp. 430-442.

Yates et al., Quantitative detection of hepatitis B virus DNA by real-time nucleic acid sequence-based amplification with; molecular beacon detection. J. of Clinical Microbiology 39(10) : 3656 (2001).

Zhou et al., "High-Resolution DNA Melting Analysis for Simultaneous Mutation Scanning and Genotyping in Solution," Clinical Chemistry, vol. 51, No. 10, 2005, pp. 1770-1777.

Sobrino et al., "SNPs in forensic genetics: a review on SNP typing methodologies," Forensic Science International 154, 181-194, 2005.

\* cited by examiner

SEQUENCE LISTING

<160> NUMBER OF SEQ ID NOS: 73

<210> SEQ ID NO 1
<211> LENGTH: 20
<212> TYPE: DNA
<213> ORGANISM: Artificial Sequence
<220> FEATURE:
<223> OTHER INFORMATION: probe

<400> SEQUENCE: 1
cctggtgttt gttccttccc                                                   20

<210> SEQ ID NO 2
<211> LENGTH: 30
<212> TYPE: DNA
<213> ORGANISM: Homo sapiens
<220> FEATURE:
<223> OTHER INFORMATION: probe

<400> SEQUENCE: 2
gcaccgggaa ggaacaaaca ccaggacgca                                        30

<210> SEQ ID NO 3
<211> LENGTH: 30
<212> TYPE: DNA
<213> ORGANISM: Homo sapiens

<400> SEQUENCE: 3
gcaccgggaa ggaataaaca ccaggacgca                                        30

<210> SEQ ID NO 4
<211> LENGTH: 41
<212> TYPE: DNA
<213> ORGANISM: Artificial Sequence
<220> FEATURE:
<223> OTHER INFORMATION: primer

<400> SEQUENCE: 4
gcaagccctc acgtagcgaa gtagaggagt ctgaatctgg a                           41

<210> SEQ ID NO 5
<211> LENGTH: 38
<212> TYPE: DNA
<213> ORGANISM: Artificial Sequence
<220> FEATURE:
<223> OTHER INFORMATION: primer

<400> SEQUENCE: 5
gcaagccctc acgtagcgaa tccctctggc gatagtca                               38

<210> SEQ ID NO 6
<211> LENGTH: 22
<212> TYPE: DNA
<213> ORGANISM: Artificial Sequence
<220> FEATURE:
<223> OTHER INFORMATION: probe

<400> SEQUENCE: 6
ttcagttata tggatgatgt gg                                                22

<210> SEQ ID NO 7
<211> LENGTH: 34
<212> TYPE: DNA
<213> ORGANISM: Artificial Sequence
<220> FEATURE:
<223> OTHER INFORMATION: artificial target sequence

```
<400> SEQUENCE: 7
caaaaccaca tcatccatat aactgaaagc caaa                                  34

<210> SEQ ID NO 8
<211> LENGTH: 34
<212> TYPE: DNA
<213> ORGANISM: Artificial Sequence
<220> FEATURE:
<223> OTHER INFORMATION: artificial target sequence

<400> SEQUENCE: 8
caaaaccaca tcatccatat aactaaaagc caaa                                  34

<210> SEQ ID NO 9
<211> LENGTH: 34
<212> TYPE: DNA
<213> ORGANISM: Artificial Sequence
<220> FEATURE:
<223> OTHER INFORMATION: artificial target sequence

<400> SEQUENCE: 9
caaaaccaca tcatccatat agctgaaagc caaa                                  34

<210> SEQ ID NO 10
<211> LENGTH: 34
<212> TYPE: DNA
<213> ORGANISM: Artificial Sequence
<220> FEATURE:
<223> OTHER INFORMATION: artificial target sequence

<400> SEQUENCE: 10
caaaaacaca tcatccatat aactgaaagc caaa                                  34

<210> SEQ ID NO 11
<211> LENGTH: 34
<212> TYPE: DNA
<213> ORGANISM: Artificial Sequence
<220> FEATURE:
<223> OTHER INFORMATION: artificial target sequence

<400> SEQUENCE: 11
caaaaccaca tcatccacat aactgaaagc caaa                                  34

<210> SEQ ID NO 12
<211> LENGTH: 34
<212> TYPE: DNA
<213> ORGANISM: Artificial Sequence
<220> FEATURE:
<223> OTHER INFORMATION: artificial target sequence

<400> SEQUENCE: 12
caaaaccaca tcatccacat aactaaaagc caaa                                  34

<210> SEQ ID NO 13
<211> LENGTH: 34
<212> TYPE: DNA
<213> ORGANISM: Artificial Sequence
<220> FEATURE:
<223> OTHER INFORMATION: artificial target sequence

<400> SEQUENCE: 13
caaaaccaca tcatccacat agctgaaagc caaa                                  34

<210> SEQ ID NO 14
```

<210> SEQ ID NO 14
<211> LENGTH: 34
<212> TYPE: DNA
<213> ORGANISM: Artificial Sequence
<220> FEATURE:
<223> OTHER INFORMATION: artificial target sequence

<400> SEQUENCE: 14
caaaaacaca tcatccacat aactgaaagc caaa                              34

<210> SEQ ID NO 15
<211> LENGTH: 34
<212> TYPE: DNA
<213> ORGANISM: Artificial Sequence
<220> FEATURE:
<223> OTHER INFORMATION: artificial target sequence

<400> SEQUENCE: 15
caaaaccaca tcatcaatat aactgaaagc caaa                              34

<210> SEQ ID NO 16
<211> LENGTH: 34
<212> TYPE: DNA
<213> ORGANISM: Artificial Sequence
<220> FEATURE:
<223> OTHER INFORMATION: artificial target sequence

<400> SEQUENCE: 16
caaaaccaca tcatcaatat aactaaaagc caaa                              34

<210> SEQ ID NO 17
<211> LENGTH: 34
<212> TYPE: DNA
<213> ORGANISM: Artificial Sequence
<220> FEATURE:
<223> OTHER INFORMATION: artificial target sequence

<400> SEQUENCE: 17
caaaaccaca tcatcaatat agctgaaagc caaa                              34

<210> SEQ ID NO 18
<211> LENGTH: 33
<212> TYPE: DNA
<213> ORGANISM: Artificial Sequence
<220> FEATURE:
<223> OTHER INFORMATION: artificial target sequence

<400> SEQUENCE: 18
caaaaacaca tcatcaatat aactgaaagc caa                               33

<210> SEQ ID NO 19
<211> LENGTH: 26
<212> TYPE: DNA
<213> ORGANISM: Artificial Sequence
<220> FEATURE:
<223> OTHER INFORMATION: probe

<400> SEQUENCE: 19
ccgtttctca tggctcagtt tactag                                       26

<210> SEQ ID NO 20
<211> LENGTH: 29
<212> TYPE: DNA
<213> ORGANISM: Artificial Sequence
<220> FEATURE:
<223> OTHER INFORMATION: primer

<400> SEQUENCE: 20

-continued ggaaactgca cttgtattcc catcccatc                                      29

<210> SEQ ID NO 21
<211> LENGTH: 25
<212> TYPE: DNA
<213> ORGANISM: Artificial Sequence
<220> FEATURE:
<223> OTHER INFORMATION: primer

<400> SEQUENCE: 21
gtttacagga agtttcctaa aacac                                          25

<210> SEQ ID NO 22
<211> LENGTH: 26
<212> TYPE: DNA
<213> ORGANISM: Artificial Sequence
<220> FEATURE:
<223> OTHER INFORMATION: probe

<400> SEQUENCE: 22
cctgataccg acgagcaagc actgga                                         26

<210> SEQ ID NO 23
<211> LENGTH: 32
<212> TYPE: DNA
<213> ORGANISM: Artificial Sequence
<220> FEATURE:
<223> OTHER INFORMATION: artificial target sequence

<400> SEQUENCE: 23
atttccagtg cttgctcgcc ggtatcaggc tg                                  32

<210> SEQ ID NO 24
<211> LENGTH: 32
<212> TYPE: DNA
<213> ORGANISM: Artificial Sequence
<220> FEATURE:
<223> OTHER INFORMATION: artificial target sequence

<400> SEQUENCE: 24
atttccagtg cttgctcgcc ggtatctggc tg                                  32

<210> SEQ ID NO 25
<211> LENGTH: 32
<212> TYPE: DNA
<213> ORGANISM: Artificial Sequence
<220> FEATURE:
<223> OTHER INFORMATION: artificial target sequence

<400> SEQUENCE: 25
atttccagcg cttgctcgcc ggtatcaggc tg                                  32

<210> SEQ ID NO 26
<211> LENGTH: 32
<212> TYPE: DNA
<213> ORGANISM: Artificial Sequence
<220> FEATURE:
<223> OTHER INFORMATION: artificial target sequence

<400> SEQUENCE: 26
atttccagtg cttgctcgcc agtatcaggc tg                                  32

<210> SEQ ID NO 27
<211> LENGTH: 32
<212> TYPE: DNA

```
<213> ORGANISM: Artificial Sequence
<220> FEATURE:
<223> OTHER INFORMATION: artificial target sequence

<400> SEQUENCE: 27
atttctagtg cttgctcgcc ggtatctggc tg                           32

<210> SEQ ID NO 28
<211> LENGTH: 32
<212> TYPE: DNA
<213> ORGANISM: Artificial Sequence
<220> FEATURE:
<223> OTHER INFORMATION: artificial target sequence

<400> SEQUENCE: 28
atttccagcg cttgctcgcc ggtatctggc tg                           32

<210> SEQ ID NO 29
<211> LENGTH: 32
<212> TYPE: DNA
<213> ORGANISM: Artificial Sequence
<220> FEATURE:
<223> OTHER INFORMATION: artificial target sequence

<400> SEQUENCE: 29
atttccagcg cttgttcgcc ggtatcaggc tg                           32

<210> SEQ ID NO 30
<211> LENGTH: 32
<212> TYPE: DNA
<213> ORGANISM: Artificial Sequence
<220> FEATURE:
<223> OTHER INFORMATION: artificial target sequence

<400> SEQUENCE: 30
atttctagcg cttgctcgcc ggtatctggc tg                           32

<210> SEQ ID NO 31
<211> LENGTH: 32
<212> TYPE: DNA
<213> ORGANISM: Artificial Sequence
<220> FEATURE:
<223> OTHER INFORMATION: artificial target sequence

<400> SEQUENCE: 31
atttccagcg cttgttcacc tgtatcaggt tg                           32

<210> SEQ ID NO 32
<211> LENGTH: 30
<212> TYPE: DNA
<213> ORGANISM: Artificial Sequence
<220> FEATURE:
<223> OTHER INFORMATION: probe

<400> SEQUENCE: 32
cactggaaat tgtgatgca ttggctcgct                               30

<210> SEQ ID NO 33
<211> LENGTH: 57
<212> TYPE: DNA
<213> ORGANISM: Artificial Sequence
<220> FEATURE:
<223> OTHER INFORMATION: artificial target sequence

<400> SEQUENCE: 33
aacgacaatc acatctaccg caccagagcg agccaatgca tcacaaattt ccagtgc    57
```

<210> SEQ ID NO 34
<211> LENGTH: 57
<212> TYPE: DNA
<213> ORGANISM: Artificial Sequence
<220> FEATURE:
<223> OTHER INFORMATION: artificial target sequence

<400> SEQUENCE: 34
aacaacaatc acatctaccg caccagagcg agccagtgca tcacaaattt ccagtgc    57

<210> SEQ ID NO 35
<211> LENGTH: 57
<212> TYPE: DNA
<213> ORGANISM: Artificial Sequence
<220> FEATURE:
<223> OTHER INFORMATION: artificial target sequence

<400> SEQUENCE: 35
aacgacgatg acatctaccg caccagagcg agccagtgca tcacaaattt ccagcgc    57

<210> SEQ ID NO 36
<211> LENGTH: 57
<212> TYPE: DNA
<213> ORGANISM: Artificial Sequence
<220> FEATURE:
<223> OTHER INFORMATION: artificial target sequence

<400> SEQUENCE: 36
aacaacaatc acatctaccg caccagagcg agccaatgca tcacaaatct ccagtgc    57

<210> SEQ ID NO 37
<211> LENGTH: 57
<212> TYPE: DNA
<213> ORGANISM: Artificial Sequence
<220> FEATURE:
<223> OTHER INFORMATION: artificial target sequence

<400> SEQUENCE: 37
aacaacaatc acatctaccg caccagaacg agccagtgca tcacaaattt ccagtgc    57

<210> SEQ ID NO 38
<211> LENGTH: 57
<212> TYPE: DNA
<213> ORGANISM: Artificial Sequence
<220> FEATURE:
<223> OTHER INFORMATION: artificial target sequence

<400> SEQUENCE: 38
aacaacaatc acatctactg caccagagcg agctagtgca tcacaaattt ccagcgc    57

<210> SEQ ID NO 39
<211> LENGTH: 57
<212> TYPE: DNA
<213> ORGANISM: Artificial Sequence
<220> FEATURE:
<223> OTHER INFORMATION: artificial target sequence

<400> SEQUENCE: 39
aacaacaatc acatctaccg caccagagcg agccagcgca tcacagattt ccagcgc    57

<210> SEQ ID NO 40
<211> LENGTH: 57
<212> TYPE: DNA
<213> ORGANISM: Artificial Sequence
<220> FEATURE:

<223> OTHER INFORMATION: artificial target sequence

<400> SEQUENCE: 40
aacgacgatg acatctaccg caccagagcg agccagcgca tcacagattt ctagcgc        57

<210> SEQ ID NO 41
<211> LENGTH: 36
<212> TYPE: DNA
<213> ORGANISM: Artificial Sequence
<220> FEATURE:
<223> OTHER INFORMATION: probe

<400> SEQUENCE: 41
attaagcaga tgcgttttcc cggttacttc ttgatc        36

<210> SEQ ID NO 42
<211> LENGTH: 59
<212> TYPE: DNA
<213> ORGANISM: Artificial Sequence
<220> FEATURE:
<223> OTHER INFORMATION: artificial target sequence

<400> SEQUENCE: 42
aactccatca cgatcaagaa gtaaccggga aacccatct ggtttatcac atcgagctc        59

<210> SEQ ID NO 43
<211> LENGTH: 59
<212> TYPE: DNA
<213> ORGANISM: Artificial Sequence
<220> FEATURE:
<223> OTHER INFORMATION: artificial target sequence

<400> SEQUENCE: 43
aactccatca cgatcaagaa gtaaccggga agcccatct ggttaatcac atcgagctc        59

<210> SEQ ID NO 44
<211> LENGTH: 59
<212> TYPE: DNA
<213> ORGANISM: Artificial Sequence
<220> FEATURE:
<223> OTHER INFORMATION: artificial target sequence

<400> SEQUENCE: 44
aactccatca cgatcaagaa gtagccggga aagcccatct ggttaatcac atcgagctc        59

<210> SEQ ID NO 45
<211> LENGTH: 59
<212> TYPE: DNA
<213> ORGANISM: Artificial Sequence
<220> FEATURE:
<223> OTHER INFORMATION: artificial target sequence

<400> SEQUENCE: 45
aactccatca cgatcaagaa gtatccggga aagcccatct ggttaatcac atcgagctc        59

<210> SEQ ID NO 46
<211> LENGTH: 59
<212> TYPE: DNA
<213> ORGANISM: Artificial Sequence
<220> FEATURE:
<223> OTHER INFORMATION: artificial target sequence

<400> SEQUENCE: 46
aactccatca cgaccaagaa gtatccggga aagcccatct ggttaatcac atcgagctc        59

```
<210> SEQ ID NO 47
<211> LENGTH: 59
<212> TYPE: DNA
<213> ORGANISM: Artificial Sequence
<220> FEATURE:
<223> OTHER INFORMATION: artificial target sequence

<400> SEQUENCE: 47
aattccatca cgatcaagaa atagccggga aagcccatct ggttgatgac atcgagctc      59

<210> SEQ ID NO 48
<211> LENGTH: 41
<212> TYPE: DNA
<213> ORGANISM: Artificial Sequence
<220> FEATURE:
<223> OTHER INFORMATION: probe

<400> SEQUENCE: 48
tgtgattaac caggctttcc cgattacttc ttgatcgtga t                         41

<210> SEQ ID NO 49
<211> LENGTH: 59
<212> TYPE: DNA
<213> ORGANISM: Artificial Sequence
<220> FEATURE:
<223> OTHER INFORMATION: artificial target sequence

<400> SEQUENCE: 49
aactccatca cgatcaagaa gtaaccggga aagcccatct ggttaatcac atcgagctc      59

<210> SEQ ID NO 50
<211> LENGTH: 59
<212> TYPE: DNA
<213> ORGANISM: Artificial Sequence
<220> FEATURE:
<223> OTHER INFORMATION: artificial target sequence

<400> SEQUENCE: 50
aactccatca cgatcaagaa gtatccggga aagcccatct ggttaatcac atcgagctc      59

<210> SEQ ID NO 51
<211> LENGTH: 59
<212> TYPE: DNA
<213> ORGANISM: Artificial Sequence
<220> FEATURE:
<223> OTHER INFORMATION: artificial target sequence

<400> SEQUENCE: 51
aactccatca cgatcaagaa gtagccggga aagcccatct ggttaattac atcgagctc      59

<210> SEQ ID NO 52
<211> LENGTH: 59
<212> TYPE: DNA
<213> ORGANISM: Artificial Sequence
<220> FEATURE:
<223> OTHER INFORMATION: artificial target sequence

<400> SEQUENCE: 52
aactccatta cgatcaagaa gtatccggga aagcccatct ggttaatcac atcgagctc      59

<210> SEQ ID NO 53
<211> LENGTH: 59
<212> TYPE: DNA
<213> ORGANISM: Artificial Sequence
<220> FEATURE:
<223> OTHER INFORMATION: artificial target sequence
```

<400> SEQUENCE: 53
aactccatca cgaccaagaa gtatccggga aagcccatct ggttaatcac atcgagctc          59

<210> SEQ ID NO 54
<211> LENGTH: 59
<212> TYPE: DNA
<213> ORGANISM: Artificial Sequence
<220> FEATURE:
<223> OTHER INFORMATION: artificial target sequence

<400> SEQUENCE: 54
aactccatca cgatcaagaa gtaaccggga aaacccatct ggtttatcac atcgagctc          59

<210> SEQ ID NO 55
<211> LENGTH: 59
<212> TYPE: DNA
<213> ORGANISM: Artificial Sequence
<220> FEATURE:
<223> OTHER INFORMATION: artificial target sequence

<400> SEQUENCE: 55
aattccatca cgatcaagaa atagccggga aagcccatct ggttgatgac atcgagctc          59

<210> SEQ ID NO 56
<211> LENGTH: 24
<212> TYPE: DNA
<213> ORGANISM: Vibrio cholerae
<220> FEATURE:
<223> OTHER INFORMATION: artificial target sequence

<400> SEQUENCE: 56
tgtgcgttta tcgatgccga gcac                                               24

<210> SEQ ID NO 57
<211> LENGTH: 20
<212> TYPE: DNA
<213> ORGANISM: Vibrio cholerae

<400> SEQUENCE: 57
gcttttggtg tcaaagccgc                                                    20

<210> SEQ ID NO 58
<211> LENGTH: 26
<212> TYPE: DNA
<213> ORGANISM: Artificial Sequence
<220> FEATURE:
<223> OTHER INFORMATION: probe

<400> SEQUENCE: 58
cctgataccg acgagcaagc actgga                                             26

<210> SEQ ID NO 59
<211> LENGTH: 20
<212> TYPE: DNA
<213> ORGANISM: Artificial Sequence
<220> FEATURE:
<223> OTHER INFORMATION: probe

<400> SEQUENCE: 59
cgggtgtttg ttccttcccg                                                    20

<210> SEQ ID NO 60
<211> LENGTH: 48
<212> TYPE: DNA
<213> ORGANISM: Artificial Sequence

```
<220> FEATURE:
<223> OTHER INFORMATION: artificial target sequence

<400> SEQUENCE: 60
accgggaagg aacaaacacc aggacgcaaa aagcacgggg ctgggctg                    48

<210> SEQ ID NO 61
<211> LENGTH: 48
<212> TYPE: DNA
<213> ORGANISM: Artificial Sequence
<220> FEATURE:
<223> OTHER INFORMATION: artificial target sequence

<400> SEQUENCE: 61
accgggaagg aataaacacc aggacgcaaa aagcacgggg ctgggctg                    48

<210> SEQ ID NO 62
<211> LENGTH: 39
<212> TYPE: DNA
<213> ORGANISM: Artificial Sequence
<220> FEATURE:
<223> OTHER INFORMATION: primer

<400> SEQUENCE: 62
gcaagccctc acgtagcgaa caatctactc ccaggagca                              39

<210> SEQ ID NO 63
<211> LENGTH: 40
<212> TYPE: DNA
<213> ORGANISM: Artificial Sequence
<220> FEATURE:
<223> OTHER INFORMATION: primer

<400> SEQUENCE: 63
gcaagccctc acgtagcgaa gcccagtttc tattggtctc                             40

<210> SEQ ID NO 64
<211> LENGTH: 40
<212> TYPE: DNA
<213> ORGANISM: Artificial Sequence
<220> FEATURE:
<223> OTHER INFORMATION: primer

<400> SEQUENCE: 64
gcaagccctc acgtagcgaa ccttaggctg ctggtggtct                             40

<210> SEQ ID NO 65
<211> LENGTH: 39
<212> TYPE: DNA
<213> ORGANISM: Artificial Sequence
<220> FEATURE:
<223> OTHER INFORMATION: primer

<400> SEQUENCE: 65
gcaagccctc acgtagcgaa gtgcccttga ggttgtcca                              39

<210> SEQ ID NO 66
<211> LENGTH: 40
<212> TYPE: DNA
<213> ORGANISM: Artificial Sequence
<220> FEATURE:
<223> OTHER INFORMATION: primer

<400> SEQUENCE: 66
gcaagccctc acgtagcgaa catcatgcct ctttgcacca                             40
```

<210> SEQ ID NO 67
<211> LENGTH: 44
<212> TYPE: DNA
<213> ORGANISM: Artificial Sequence
<220> FEATURE:
<223> OTHER INFORMATION: primer

<400> SEQUENCE: 67
gcaagccctc acgtagcgaa gcaatatgaa acctcttaca tcag          44

<210> SEQ ID NO 68
<211> LENGTH: 25
<212> TYPE: DNA
<213> ORGANISM: Artificial Sequence
<220> FEATURE:
<223> OTHER INFORMATION: probe

<400> SEQUENCE: 68
cggctgggca taaaagtcag ggccg                               25

<210> SEQ ID NO 69
<211> LENGTH: 28
<212> TYPE: DNA
<213> ORGANISM: Artificial Sequence
<220> FEATURE:
<223> OTHER INFORMATION: probe

<400> SEQUENCE: 69
cacgttcctg tggggcaagg tgaacgtg                            28

<210> SEQ ID NO 70
<211> LENGTH: 31
<212> TYPE: DNA
<213> ORGANISM: Artificial Sequence
<220> FEATURE:
<223> OTHER INFORMATION: probe

<400> SEQUENCE: 70
cggtgaggcc cttggcaggt tggtatcacc c                        31

<210> SEQ ID NO 71
<211> LENGTH: 32
<212> TYPE: DNA
<213> ORGANISM: Artificial Sequence
<220> FEATURE:
<223> OTHER INFORMATION: probe

<400> SEQUENCE: 71
cgatccaggt tctttgagtc ctttggggat cg                       32

<210> SEQ ID NO 72
<211> LENGTH: 25
<212> TYPE: DNA
<213> ORGANISM: Artificial Sequence
<220> FEATURE:
<223> OTHER INFORMATION: primer

<400> SEQUENCE: 72
cctcggtgcc tttagtgatg gccga                               25

<210> SEQ ID NO 73
<211> LENGTH: 26
<212> TYPE: DNA
<213> ORGANISM: Artificial Sequence
<220> FEATURE:
<223> OTHER INFORMATION: primer

<400> SEQUENCE: 73
ctgggttaag gtaatagcaa taccca                                    26

METHOD FOR DETECTING VARIATIONS IN NUCLEIC ACID SEQUENCES

This application is a division of Ser. No. 13/322,716, which is the U.S. national stage entry of PCT/CN2010/000753 filed on May 26, 2010, which claims priority of the Chinese patent applications No. 200910143480.6 filed on May 26, 2009 in the name of Xiamen University, this priority application is incorporated herein in its entirety by reference, as if the entire contents thereof are explicitly described in the present application.

This application incorporates by reference the contents of a 13.2 kb text file created on Nov. 28, 2011 and named "PCTCN2010000753sequencelisting.txt," which is the sequence listing for this application.

FIELD OF THE INVENTION

The present invention relates to a method for detecting nucleic acid sequence variation, as well as to probes and kits for said method. Particularly, it relates to a method for detecting nucleic acid sequence variation by self-quenched probe-based melting curve analysis, and to self-quenched probes and kits.

TECHNICAL BACKGROUND

Melting curve analysis for detecting nucleic acid sequence variation is to include an additional temperature increasing step (sometimes may also be a temperature decreasing step) in the real-time PCR program, then, information about amplification products or sequence variations can be detected by recording the change of fluorescence with the change of temperature. The current melting temperature analysis includes three types, namely the fluorescent dye method, the fluorescent probe-based method, and the fluorescent dye-fluorescent probe combination method.

The principle of the fluorescent dye method is very simple, wherein a dye (such as SYBR Green, SYTO-9, or LC Green) capable to bind double-stranded DNA molecules to give rise to fluorescence is added into the PCR system. An increase in temperature leads to denaturation of the double-stranded DNA, resulting in a decrease of fluorescence. A sequence variation can be indicated as a change in melting temperature (Wittwer C. T., et al, BioTechniques, 1997, 22:130-138; Ririe K. M., et al, Anal. Biochem, 1997, 245:154-160; US Patent US 2006/0019253 A1); US Patent, US 2003/0224434 A1). Specifically, single nucleotide changes can be detected in combination with High Resolution Melting (HRM) analysis (Wittwer C. T., et al, Clin Chem, 2003, 49: 853-860). Fluorescent probe-based method is using probes to detect sequence variations at a specific site, provided that the probe can give rise to a specific fluorescence signal upon hybridizing to a target sequence. There are various types of such probes in real-time PCR, but few probes are available for melting curve analysis, among them, the most well-known is the Fluorescence Resonance Energy Transfer (FRET) probe, also called LightCycler™ probe or adjacent hybridization probe (U.S. Pat. No. 7,160,998 B2; U.S. Pat. No. 6,472,156 B1; U.S. Pat. No. 6,140,054). Others use oligonucleotide probes with a single label (U.S. Pat. No. 6,635,427 B2), HyBeacon (US Patent, US 2008/0311579 A1) probe, etc. A fluorescent dye and fluorescent probe in combination method is a method wherein either a fluorescence-enhancing or a fluorescence-quenching dye is added simultaneously with a fluorescent probe, such as in the so-called induced fluorescence resonance energy transfer (iFRET) technology (U.S. Pat. No. 7,179,589 B2), wherein a fluorescent intercalating dye is added simultaneously with a single-labeled fluorescent probe. In such a case, the fluorescent intercalating dye binds to double-stranded DNA and the fluorescence emitted can increase the fluorescence of the fluorescently labeled probe by energy transfer. An increase in temperature makes the probe dissociate from the target sequence, thereby decreasing the hypersensitive fluorescence. Gupta et al. (US Patent, US 2007/0020665 A1) disclosed a way for molecular subtyping of the hepatitis C virus, wherein a fluorescence quenching dye and a fluorescently labeled probe are added to the PCR reaction simultaneously. The fluorescence is quenched upon hybridization, an increase in temperature makes the probe dissociate from the target sequence, thereby allowing the quenched fluorescence to recover and resulting in the fluorescence increase.

Among the three types of melting curves discussed above, the dye method employs a single fluorescence channel for detection, and it is presently mainly used for the identification of amplification products. In combination with HRM, it is used for detection of random mutations in the amplified sequence rather than for detection of mutations at a specific site. Even rarer is it used for detection of multiple mutations occurring at multiple specific sites. The fluorescent dye and fluorescent probe in combination method (regardless whether this combination involves fluorescence enhancing format or fluorescence quenching format) is limited to certain special fluorescent dyes, and the number of fluorescence channels that can be used for detection of this format of labeling is limited, so as to the number of sites that can be detected. Thus, few application examples involving this dye-probe combination method exist.

The most successful example of the probe-based method is LightCycler™ probe. LightCycler™ probe consists of two specific probes that are complementary to an adjacent region of the template. One probe is labeled with a donor fluorophore (referred to as detection probe) and the other is labeled with an acceptor fluorophore (referred to as anchor probe). The melting temperature of the detection probe is approximately 10° C. lower than that of the anchor probe. FRET should take place between the donor fluorophore and the acceptor fluorophore. In the absence of a target sequence, the two probes are separated and stay in a free state, and the acceptor fluorophore group cannot be excited, thereby generating no FRET signal. In the presence of a complementary target sequence, the two probes bind to the complementary template simultaneously, which brings the donor fluorophore group and the acceptor fluorophore group close to each other. The fluorescence energy generated by the donor fluorophore group is absorbed by the acceptor group, resulting in a fluorescence signal of a specific wavelength, and a FRET signal becomes detectable. When the temperature increases, the detection probe dissociates from the template first, and a specific melting temperature could be detected. When a sequence variation exists in target sequence that is hybridized with the detection probe, the degree of variation will affect the temperature of probe dissociation, resulting in a different melting temperature. Based on this, whether and in which specific form a sequence variation occurs in the detection probe-covered regions of the target could be determined. Since the LightCycler™ technology requires an anchor probe that is actually not used for detecting sequence variations, the area covered by the anchor probe will become a blind area for detection. When sequence variation exists in a wide range, the selection of a conserved region for the anchor probe would become difficult. In addition, since LightCycler™ probe employs the detection of FRET, a suitable wavelength combination of fluorescence donor and acceptor would be required for FRET to take place. However, only limited combinations of fluorescence donor and acceptor are currently available for carrying out effective FRET. Meanwhile, the optical channel for the detection of FRET is different from that for detection of conventional, single fluorescent dyes: with the exception of the dedicated instruments, most mainstream real-time PCR machines can not be used for the detection of FRET. Moreover, the number of channels useful for detecting FRET is limited as well, making the FRET technology greatly restrained in the application of detecting multiple genes in a single tube.

In the probe-based method, both the single-labeled oligonucleotide probe and the HyBeacon probe are oligonucleotide probes labeled only with a fluorescent group, and change of fluorescence intensity would occur after hybridization of the probe to a target. Both probes are useful in melting curve analysis, whereby nucleic acid sequence variation is detected via changes in of the melting temperature. However, in this fluorophore only single-labeling manner, no quencher group exists and quenching efficiency of the probes depends on specific nucleic acid sequence or the guanine residue. That makes the fluorescence background relatively high, changes in fluorescence intensity after hybridization being limited, and the signal to noise ratio is low. Moreover, in the case of the HyBeacon probe, the fluorescent group is labeled internally, making it difficult to synthesize and label the probes, thereby restricting wide application of such probes in the detection of nucleic acid sequence variation by melting curve analysis.

In the probe-based method, there is also a type of dual-labeled probes containing minor groove binder (MGB), especially probes with the MGB located in the 5' end, such as MGB-Eclipse probe (Afonina, I. A., et al, Biotechniques, 2002, 32: 940-944, 946-949) and Pleiades probe (Lukhtanov, E. A., et al, Nucleic Acids Res, 2007, 35: e30). Since such probes can resist the 5'-hydrolysis activity of thermostable DNA polymerase (e.g., Taq polymerase), they have also been reported to be useful in melting curve analysis. MGB group in this kind of probes may act to increase the melting temperature. The aim of this design is to shorten the probe while maintaining a relatively high melting temperature, but for a mismatched target sequence, the melting temperature will decrease a lot. Thus, it is mainly used to specifically detect the matched target sequence, rather than being used for a melting curve analysis for mutation detection. This is because the latter requires that both the matched and mutated target sequences to be differentiated through different melting temperatures, and it is not necessary that the mismatched target sequence has a very low melting temperature. In addition, the synthesis of this kind of probes is more difficult and more expensive than the synthesis of probes without MGB.

Thus, a novel fluorescent probe is needed for melting curve analysis in order to achieve simultaneous detection of multiple variations in a single tube. Preferably, such a fluorescent probe can be labeled with common fluorescent groups, and can perform multi-color analysis in a commonly used real-time PCR machine. Such a probe is also preferably suitable for the melting curve analysis of nucleic acid amplification products, for example, it will not be degraded or is only degraded minimally under the conventional PCR-cycle reaction conditions, in order to maintain sufficient amount of intact fluorescent probes for subsequent melting curve analysis. More preferably, such a probe shall be easily synthesized, not involving complicated and expensive chemical modifications, thereby lowering the cost for use.

DETAILED DESCRIPTION OF THE INVENTION

In one aspect, the present invention provides a method for detecting target nucleic acid sequence variations by performing melting curve analysis using a self-quenched probe. Said probe are labeled with a fluorescent group and a quenching group, and under the reaction conditions provided by the present invention, melting curve analysis can be performed after nucleic acid amplification, to detect variations in a target sequence.

The method provided by the present invention comprises the use of a self-quenched probe and the corresponding experimental conditions of using such self-quenched probe to perform melting curve analysis.

Said self-quenched probe generally refers to an oligonucleotide probe, with one end labeled by a fluorescent group and the other end labeled by a quenching group. Fluorescence intensity increases when said probe hybridizes with a target nucleic acid sequence. Said probe may be labeled at the 5' end with a fluorescent group and at the 3' end with a quenching group. Alternatively, said probe may be labeled at the 3' end with a fluorescent group and at the 5' end with a quenching group. When said probe is present alone, the fluorescent group and the quenching group is close to and thus interacts with each other, so that the fluorescence emitted by the fluorescent group is absorbed by the quenching group, leading to a decrease in the fluorescence of the probe. When said probe hybridizes to its target sequence, the fluorescent group is apart from the quenching group, so that the fluorescence emitted by the fluorescent group cannot be absorbed by the quenching group, thereby increasing the fluorescence of the probe.

The sequence of the probe used in the present invention comprises the following sequences: the fully complementary sequence of a wild type or variant target nucleic acid sequence; or alternatively, a sequence comprising several (such as 1-10, 1-5, 1-4, 1-3, 1-2, 1 or 2) mismatches, such as one or more (e.g. 1-10, 1-5, 1-4, 1-3, 1-2, 1 or 2) conversion, transversion, insertion and/or deletion of a single base comparing to the fully complementary sequence of a wild type or variant target nucleic acid sequence.

The sequence of the probe used in the present invention may completely be or comprise a complementary sequence of its target sequence. Alternatively, it may be a sequence comprising one or more conversions, transversions, insertions or deletions of a single base comparing to the perfect complement sequence of a wild type or variant target nucleic acid sequence.

The melting curve analysis may generally comprise the following steps: after nucleic acid amplification, a probe bound to a target sequence dissociates from the target sequence and results in changes of fluorescence intensity as the temperature increases; obtaining a melting curve by plotting the rate of fluorescence intensity change (as y axis) as a function of changing temperature (x axis); by detecting during this process, in real-time, the changes of fluorescence intensity with the change of the temperature, variations of the target sequences may be detected using this melting curve. The melting curve mentioned above may also be obtained in a manner of decreasing the temperature, namely from high temperature to low temperature, to detect fluorescence changes. Melting curve analysis is then performed by processing the data obtained.

Said corresponding experimental conditions for performing the melting curve analysis refers to conditions enabling the self-quenched probe to achieve melting curve analysis, preferably, the conditions include one or several of the following conditions:

1) Using asymmetric PCR, which means that during the reaction, one primer is relatively in excess, and the strands resulting from the elongation of said excess primer hybridize with the probe;
2) Thermostable DNA polymerase having no exonuclease activity or very low exonuclease activity is used in the PCR amplification;
3) The probe itself contains a chemical modification that is resistant to the exonuclease activity of the DNA polymerase; and/or
4) The probe has a hairpin structure, either a natural hairpin structure probe or an artificial hairpin structure, but mostly an artificial hairpin structure probe, namely an artificial hairpin structure formed by artificially adding bases unrelated to the target sequence at the terminal of the probe. The principle for adding such bases unrelated to the target sequence is that in the arm sequence of the so formed hairpin structure, part of or all of the bases are complementary to the target sequence, and thereby forming an arm with a length in general of 2-15 bases, preferably 3-7 bases, more preferably 4-7 bases or 4-6 bases.

Another object of the present invention is to provide a method for the homogeneous detection of nucleic acid sequence variation. Said method is accomplished with melting curve analysis, and the melting curve analysis employs a probe-based method. The probe used in the present invention is linear or has a hairpin structure, and said probe is completely or partially complementary to the target sequence, in addition, the 5' and 3' terminals of the probe are labeled with a fluorescent group and a quenching group, respectively. The probe is characterized by the fact that its fluorescence increases upon binding to the target sequence. This kind of probe is referred to as a self-quenched probe, meaning that the fluorescence is relatively weak when the probe is present alone; however, the fluorescence increases upon hybridizing with its target sequence. The melting curve analysis and the corresponding technical solutions are designed in a region where nucleic acid sequence variation needs to be detected, and the corresponding self-quenched probe is prepared. Then, after an amplification reaction, with the melting curve analysis of the self-quenched probe, the presence of a nucleic acid sequence variation in the region of interest can be determined based on changes in the melting temperature.

Another object of the present invention is to provide a method for simultaneously detecting nucleic acid sequence variations in many different regions. The technical strategy thereof is to design and prepare a self-quenched probe directing at each region, respectively, and each self-quenched probe is labeled with a different fluorescent group. After an amplification reaction, with melting curve analysis of the self-quenched probes, the presence of a nucleic acid sequence variation in a corresponding region can be determined based on the change in the melting temperature detected by each self-quenched probe.

In another aspect, the present invention provides a self-quenched nucleic acid probe useful for detecting target nucleic acid sequence variation (preferably for detecting target nucleic acid sequence variation via melting curve analysis). Said probe is labeled with a fluorescent group and a quenching group, so that comparing to the situation when a target nucleic acid sequence is absent, fluorescence (or fluorescence intensity) increases upon the hybridization of the probe with a target nucleic acid sequence. Preferably, the probe contains a modification able to resist the exonuclease activity of a DNA polymerase.

Another aspect of the present invention is to provide a self-quenched probe, wherein:

The 5' end of said probe may be labeled with a fluorescent group and the 3' end may be labeled with a quenching group; alternatively, the 3' end of said probe may be labeled with a fluorescent group and the 5' end may be labeled with a quenching group.

When the probe is present alone, the fluorescent group and the quenching group are close to and interact with each other, so that the fluorescence emitted by the fluorescent group is absorbed by the quenching group, resulting in a decrease of the fluorescence of the probe; but when the probe hybridizes with its target nucleic acid sequence, the fluorescent group is apart from the quenching group, so that the fluorescence emitted by the fluorescent group cannot be absorbed by the quenching group, thereby increasing the fluorescence of the probe; and The sequence of the probe can be the fully complementary sequence of its target nucleic acid sequence; or alternatively, it can be a sequence comprising one or more (such as 1-10, 1-5, 1-4, 1-3, 1-2, 1 or 2) mismatches, such as one or more (e.g. 1-10, 1-5, 1-4, 1-3, 1-2, 1 or 2) conversions, transversions, insertions and/or deletions of a single base comparing to the fully complementary sequence of the target nucleic acid sequence.

Another objection of the present invention is to provide a kit for detecting nucleic acid variation using a self-quenched probe dependent melting curve analysis, said kit comprises one or more of the following: a primer for target sequence amplification, a self-quenched probe, and optionally other components necessary for nucleic acid amplification reaction, including a thermostable nucleic acid polymerase, mononucleotide, buffer, metal ion, and a buffer with an appropriate acidity.

Generally, the present invention may comprise the following steps:
1) Design and prepare a corresponding self-quenched probe in a region where nucleic acid sequence variation needs to be detected;
2) Amplify the fragment comprising the region to be detected;
3) Performing the melting curve analysis after amplification, determining whether a variation is present in the nucleic acid sequence to be tested and the possible types of the variation based on differences in the melting temperature detected by the self-quenched probe.

In a specific aspect, a method for detecting nucleic acid sequence variation is provided. Said method comprises: 1) design and prepare a corresponding self-quenched probe in a region where nucleic acid sequence variation needs to be detected; the 5' end of said probe is labeled with a fluorescent group (or a quenching group) and the 3' end is labeled with a quenching group (or a fluorescent group); when necessary, the probe needs to employ chemical modifications and structural modifications beneficial to melting curve analysis; 2) amplify by PCR the fragment comprising the region to be tested with a suitable primer, the PCR amplification needs to be performed under conditions beneficial to melting curve analysis; 3) melting curve analysis is carried out after the PCR reaction, the presence of a variation in the nucleic acid sequence to be tested and the possible type of the variation is determined based on differences in the melting temperature detected by the self-quenched probe.

Said nucleic acid sequence variation refers to change of a base, which can be changes of a single base, or changes of two or more bases, including conversions, transversions, additions and deletions of a base.

When appropriate, as used herein, the term "nucleotide" and "base" can be used interchangeably, and it may be modified or unmodified.

Said region where nucleic acid sequence variation needs to be detected can be one region of multiple regions.

Said self-quenched probe is an oligonucleotide probe or a DNA analog probe, whose melting temperature shall not be lower than the melting temperature of the primer, and the length thereof is generally 10-100 bases, preferably 20-60 bases.

Structurally, said self-quenched probe can be a single-stranded linear probe, but it may also contain a secondary structure, in particular a hairpin structure; the hairpin structure may be a natural hairpin structure probe or an artificial hairpin structure, but mostly an artificial hairpin structure probe, namely an artificial hairpin structure formed by artificially adding bases unrelated to the target sequence at the terminal of the probe. The principle for adding such bases unrelated to the target sequence is that in the arm sequence of the so formed hairpin structure, part of or all of the bases are complementary to the target sequence, and thereby forming an arm with a length in general of 2-15 bases, preferably 3-7 bases, more preferably 4-7 bases or 4-6 bases.

When the probe is present alone, the fluorescent group and the quenching group are close to and interact with each other, so that the fluorescence emitted by the fluorescent group is absorbed by the quenching group, resulting in a decrease of the fluorescence of the probe; but when the probe hybridizes with its target nucleic acid sequence, the fluorescent group is apart from the quenching group, so that the fluorescence emitted by the fluorescent group cannot be absorbed by the quenching group, thereby increasing the fluorescence of the probe.

Said self-quenched probe distinguishes the wild type target sequence from the variant target sequence through changes of the melting temperature (or melting curve), the probe can be designed to be completely complementary to the wild type target sequence, or can be completely complementary to a variant target sequence. Meanwhile, to achieve this aim, mismatched bases may be introduced into the sequence of the probe.

Said self-quenched probe is labeled at the 5' end with a fluorescent group (or a quenching group) and at the 3' end with a quenching group (or a fluorescent group); thus, when the probe is not hybridized with the target sequence, the fluorescent group and the quenching group interacts with each other, so that the fluorescence emitted by the fluorescent group is absorbed by the quenching group, therefore, the fluorescence of the probe itself is very weak; when the probe hybridizes with the target sequence, a double-stranded structure can be formed, rendering the fluorescent group being separated from the quenching group, thus, the fluorescence emitted by the fluorescent group cannot be absorbed by the quenching group, thereby increasing the fluorescence after the hybridization of the probe.

Currently, said fluorescent groups include various fluorescent markers, such as ALEX-350, FAM, VIC, TET, CAL Fluor® Gold 540, JOE, HEX, CAL Fluor Orange 560, TAMRA, CAL Fluor Red 590, ROX, CAL Fluor Red 610, TEXAS RED, CAL Fluor Red 635, Quasar 670, CY3, CY5, CY5.5, Quasar 705 etc.

Currently, said quenching group includes various quenching agents, such as DABCYL, BHQs (e.g. BHQ-1 or BHQ-2), ECLIPSE, and/or TAMRA etc.

Generally, said self-quenched probe consists of common bases, however, it could also comprise bases with specific modifications. These bases with specific modifications can help with the regulation of the binding activity of the probes, for example, by increasing or decreasing the binding activity of a probe, by increasing the flexibility of the melting curve analysis. For example, a specifically modified base able to increase the binding activity of a probe (such as a locked nucleic acids (LNA) base), or a general binding base (e.g. I) able to decrease the binding activity. Therefore, in one embodiment, the probe of the present invention may consist of unmodified bases. In a preferred embodiment, the base of the probe is modified. In one preferred embodiment, the probe of the present invention comprises bases able to increase or decrease the binding activity of the probe. In another preferred embodiment, said base able to increase the binding activity of the probe includes a locked nucleic acid base. In yet one preferred embodiment, said base able to decrease the binding activity of the probe includes a general binding base, such as an I.

In a preferred embodiment, when using a DNA polymerase having a 5'→3' exonuclease activity for the PCR amplification, the self-quenched probe can be modified to resist the 5'→3' exonuclease activity of the DNA polymerase; when using a DNA polymerase having a 3'→5' exonuclease activity for the PCR amplification, the probe can be modified to resist the 3'→5' exonuclease activity of the DNA polymerase probe. Thus, during the entire amplification reaction, the integrity of the probe is maintained, making it possible to perform subsequent hybridization reaction and melting curve analysis.

Said modification able to resist the 5'→3' exonuclease activity of a DNA polymerase is preferably by means of enabling the 5' end of the probe to be resistant to the 5'→3' exonuclease activity of a nucleic acid polymerase, the way of modification includes modifying the linkage between the 5' end bases, using modified base derivatives (such as locked nucleic acid (LNA), or increasing chemical functional groups, etc. One preferred manner is to modify the linkage between the 5' end bases, for example, by using an exonuclease activity resistant linkage, such as a phosphorothioated linkage, a methylphosphonate linkage, a boranophosphated linkage, a peptide nucleic acid linkage, etc. The preferred manner is to use a phosphorothioated linkage modification, said modification being between the first and the second base of the 5' end.

Said modification able to resist the 3'→5' exonuclease activity of a DNA polymerase is preferably by means of enabling the 3' end of the probe to be resistant to the 3'→5' exonuclease activity of a nucleic acid polymerase, the way of modification includes modifying the linkage between the 3' end bases, using modified base derivatives (e.g., locked nucleic acid), or increasing chemical functional groups, etc. One preferred manner is to modify the linkage between the 3' end bases, for example, by using an exonuclease activity resistant linkage, such as a phosphorothioated linkage, a methylphosphonate linkage, a boranophosphated linkage, a peptide nucleic acid linkage, etc. The preferred manner is to use a phosphorothioated linkage modification, with said modification being between the first and the second base of the 3' end.

In a preferred embodiment, the probe may also include a secondary structure beneficial to melting curve analysis, preferably a hairpin structure, in particular a hairpin structure with the end of the probe forming an arm structure. To form such an arm structure, in most cases, an artificial hairpin structure needs to be formed by adding artificially to the end of a probe bases unrelated to the target sequence. Specifically, certain number of bases unrelated to the target sequence are added one or both end of a probe, so that an artificial hairpin structure is formed with the two ends. The principle for adding such bases unrelated to the target sequence is that in the arm sequence of the hairpin structure, part of or all of the bases are complementary to the target sequence, and thereby forming an arm with a length in general preferably of 2-15 bases, preferably 3-7 bases, more preferably 4-7 bases or 4-6 bases. The aim thereof is to ensure that the hybridization between the hairpin structure and the target sequence is carried out with sufficient efficiency, thereby can be effectively used for melting curve analysis. The advantage of using a hairpin probe to perform melting curve analysis is that, in most circumstances, under the same reaction conditions, a hairpin probe is more tolerant than a linear probe to enzyme digestion, and the background signal with a hairpin probe is lower than with a linear probe.

In a preferred embodiment, said amplification conditions beneficial to melting curve analysis include using asymmetric amplification, wherein the primer whose elongation product hybridizes with the probe is 2-100 times, preferably 2-50 times more in amount than another primer.

In a preferred embodiment, said amplification conditions beneficial to melting curve analysis further include those conditions maintaining the integrity of the probe after amplification, since the probe is added in to the reaction tube before amplification. For example, when the probe itself lacks the ability of resisting the 5'- and 3'-exonuclease activity of the enzyme, thermostable nucleic acid polymerases lacking the 5'- and 3'-exonuclease activity, such as KlentTaq, may be used; alternatively, thermostable nucleic acid polymerases having very low 5'-exonuclease activity and no 3'-exonuclease activity, such as Taq FS, may be used. There are many enzymes having said properties, and in specific experiments, choices may be made according to the requirements discussed above.

In one embodiment, the nucleic acid region to be tested in the probe of the present invention may be a single region comprising an allelic nucleic acid sequence to be tested having one or more mononucleotide variations.

In one preferred embodiment, there may be two or more nucleic acid regions to be tested in the probe of the present invention, each of these regions comprises an allelic nucleic acid sequence to be tested having one or more mononucleotide variations. Preferably, a corresponding self-quenched probe is designed and prepared for each of these regions, and each self-quenched probe is labeled with an identical or different fluorescent group; after the amplification reaction, with the melting curve analysis of the self-quenched probe, the presence of a nucleic acid sequence variation in the corresponding region can be determined based on changes in the melting temperature of each self-quenched probe.

In a detection system, there could be one or more self-quenched probes of the present invention. When multiple self-quenched probes are used, they could be labeled with different fluorescent labeling groups, so that the different self-quenched probes can be differentiated from each other; alternatively, the probes may also be labeled with the same fluorescent labeling group, and different self-quenched probes may be differentiated from each other by the differences of melting temperature after the hybridization of the probes with the allelic nucleic acid sequences to be tested; furthermore, different self-quenched probes may be differentiated from each other by using different fluorescent labeling groups in combination with different melting temperatures, thereby achieving the aim of increasing the number of regions to be tested.

The length of the probe of the present invention is generally 5-100 bases, such as 10-100, 10-50, 15-50, 20-50, 10-40 bases, and preferably, for example, 10-20, 20-30, 30-40, 15-30, 20-40, 15-25 bases.

The basic principle of the present invention is as follows:

Although the hypothetical principle of the present invention is described below, the scope of the present invention is not limited by the restrictions of these principles.

During thermal denaturation of DNA, the temperature when 50% of the DNA denatures and melts is referred to as the dissociation temperature of double-stranded DNA, also called melting temperature or melting point (Tm). Under the precondition of a given solvent, the Tm of a double-stranded DNA is fixed. When the two strands of DNA are completely complementary, the double-stranded structure formed is relatively stable, and thus the temperature required for melting the two strands of DNA is relatively high, resulting in a relatively high Tm; when the two strands of DNA are not completely complementary, the double-stranded structure formed is relatively unstable, and thus the temperature required for melting the two strands of DNA is relatively low, resulting in a relatively low Tm. In addition, the extent to which Tm decreases depends on the specific sequences that are not completely complementary.

Based on the above theory, when a double-stranded structure is formed by the hybridization of a probe with a completely matched target, the double-stranded structure thus formed has a relatively high Tm; and when the probe hybridizes with a target that is not completely matched, the double-stranded structure formed has a relatively low Tm. Therefore, if changes of Tm values can be detected, it would be possible to determined whether a variation exists in the target nucleic acid sequence, or even the specific type of said variation.

For a fluorescently labeled probe to be used in the detection of nucleic acid sequence variation, the following three conditions need to be met: 1) there must be a change in the fluorescence intensity before and after the hybridization of the probe with a target sequence; 2) the probe needs to stay intact during amplification, to be used for the melting curve analysis after amplification; 3) the specificity of a probe cannot be too high, otherwise it would be difficult for a nucleic acid sequence having a variation to hybridize with the probe. The self-quenched probe of the present invention can very well meet the three conditions described above. During melting curve analysis, the self-quenched probe hybridizes with a target sequence in the low temperature stage, when the probe and the target form a rigid and stable double-stranded structure. Since the fluorescent group is relatively far from the quenching group after probe-target hybridization, the fluorescence emitted by the fluorescent group cannot be absorbed by the quenching group, making it possible to detect a very strong fluorescence signal. As the temperature increases, the probe gradually dissociates from the target; the dissociated probe is in a single-stranded free curling state, on the probe, the labeled fluorescent group and the quenching probe are close to each other; the fluorescence emitted by the fluorescent group is absorbed by the quenching group; therefore, only a weak fluorescence signal can be detected. By detecting the fluorescence signal of a self-quenched probe during melting curve analysis, it would be possible to observe the hybridization and dissociation process between a probe and a target, and thereby forming a curve wherein the fluorescence intensity changes with the change of the temperature (namely a melting curve of the probe), and then by carrying out a derivation analysis of the melting curve, it would be possible to find the point where the biggest fluorescence change occurs, the corresponding temperature is the Tm of the probe. When a probe hybridizes with a completely matched target, the double-stranded structure formed has the highest Tm; and when a probe hybridizes with target having various sequence variations, the double-stranded structure formed has a relatively low Tm, different types of variation may result in different Tm value. Thus, the method of self-quenched probe melting curve can be used to detect nucleic acid sequence variations.

Therefore, according to the present invention, by using a melting curve, it would be possible to obtain the melting temperature of a hybrid formed between a probe and the nucleic acid to be tested; according to the melting temperature, it would be possible to detect a variation in the nucleic acid to be tested.

Alternatively, preferably, according to the present invention, by using a melting curve, it would be possible to obtain the melting temperature of a hybrid formed between a probe and the nucleic acid to be tested and the melting temperature of a hybrid formed between a probe and a reference nucleic acid; according to the difference between these two melting temperatures, it would be possible to detect a variation in the nucleic acid to be tested. A reference nucleic acid may be the wild type nucleic acid, for example.

Preferably, the melting temperature of the hybrid formed between a probe and the nucleic acid to be tested and between a probe and a reference nucleic acid is obtained with the same amplification reaction; alternatively, the melting temperature of the hybrid formed between a probe and the nucleic acid to be tested and between a probe and a reference nucleic acid is obtained by using the same melting curve to test the reactants. More preferably, a single amplification reaction comprises at least one probe, at least one reference nucleic acid and multiple nucleic acids to be tested, thereby detecting multiple nucleic acid variations. More preferably, a single amplification reaction comprises multiple probes, at least one reference nucleic acid and multiple nucleic acids to be tested, thereby detecting multiple variations existing in multiple nucleic acids to be tested. Preferably, said multiple probes are labeled with different fluorescent groups. Said multiple probes may be at least 2, 3, 5, 7, 10, 15 or 20, and at most 10, 15, 20, 30 or 50 or more, such as 2-5, 2-10, 2-20, 5-10 or 5-20. Said multiple nucleic acids to be tested may be for example, at least 2, 3, 5, 7, 10, 15 or 20, and at most 10, 20, 50 or 100 or more, such as 2-10, 2-20, 2-50. Said multiple variations may be for example at least 2, 3, 5, 7, 10, 15, 20, 30, 50 or 100, and at most 10, 20, 50, 100 or 200 or more, such as 5-10, 5-20, 5-50, 10-50, 10-100 or 10-200.

Comparing to the nucleic acid sequence variation detection techniques in the prior art, the present invention has the following prominent advantages:

1) This technology belongs to a homogeneous detection system, only simple melting curve analysis is needed after the PCR amplification to accomplish the detection, and during the whole process, the lid may not need to be open. The melting curve analysis may be performed in the same fluorescence PCR machine, or the amplification may be performed first in an ordinary PCR machine and then switching to a real-time PCR machine to perform the melting curve analysis. Therefore, the operation is easy and flexible; in addition, the whole process is carried out with the tube closed and thus would be less vulnerable to contamination.

2) This technique overcomes the limitations of the number of gene mutations that can be directly detected by real-time PCR. For example, currently, modes for detecting sequence variations employ probes such as TaqMan probe, molecular beacon, displacing probe, scorpion primer etc., wherein one sequence requires one specific detection probe. Different from that, the method provided by the present invention uses only one self-quenched probe to simultaneously detect multiple sequence variations in the region it covers.

3) Comparing to the existing probe techniques useful for melting curve analysis (such as FRET probe, single-labeled oligonucleotide probe, HyBeacon probe), this technique has the following advantages: easy to synthesize and purify (labeling a probe in the terminals is the most commonly employed approach), the fluorescence background is relatively low and the signal-to-noise ratio is relatively high (the probe is able to quench itself), easy to perform multiple detections (labeling with multiple different fluorescent groups, each fluorescent group corresponds to one probe, multiple probes may be added into one reaction tube), the cost for detection is low (one probe can be used to examine multiple variation sites that it covers).

FIGURE LEGEND

FIG. 1 shows the melting curve of self-quenched probes in the presence of various target sequences. The left panel shows corresponding changes in the fluorescence of self-quenched probes with changes of temperature. The right panel (i.e. melting curve) is obtained by making a derivation of the changes of temperature v.s. fluorescence intensity as shown in the left panel and taking the negative value thereof (−dF/dT), it directly reflects the melting temperature of a self-quenched probe in the presence of various target sequences. The long dash lines in the figure indicate matched target sequence (target 1); solid lines indicate single base mismatched target sequence (target 2); dotted dash lines indicate the absence of a target sequence.

Figure 2:
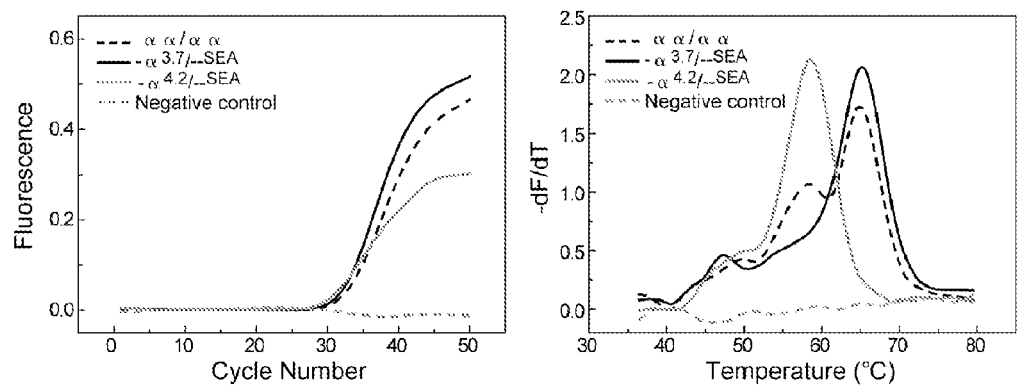

FIG. 2 shows the specimen of self-quenched probes detecting different genotypes. The left panel is the result of self-quenched probe real-time PCR detection; and the right panel is the melting curve analysis result for the self-quenched probes after PCR. In the figure, black dash lines indicate the αα/αα genotype, black solid lines indicate the $-\alpha^{3.7/--SEA}$ genotype, grey solid lines indicate the $-\alpha^{4.2/--SEA}$ genotype, and grey dash lines indicate the negative control.

Figure 3:
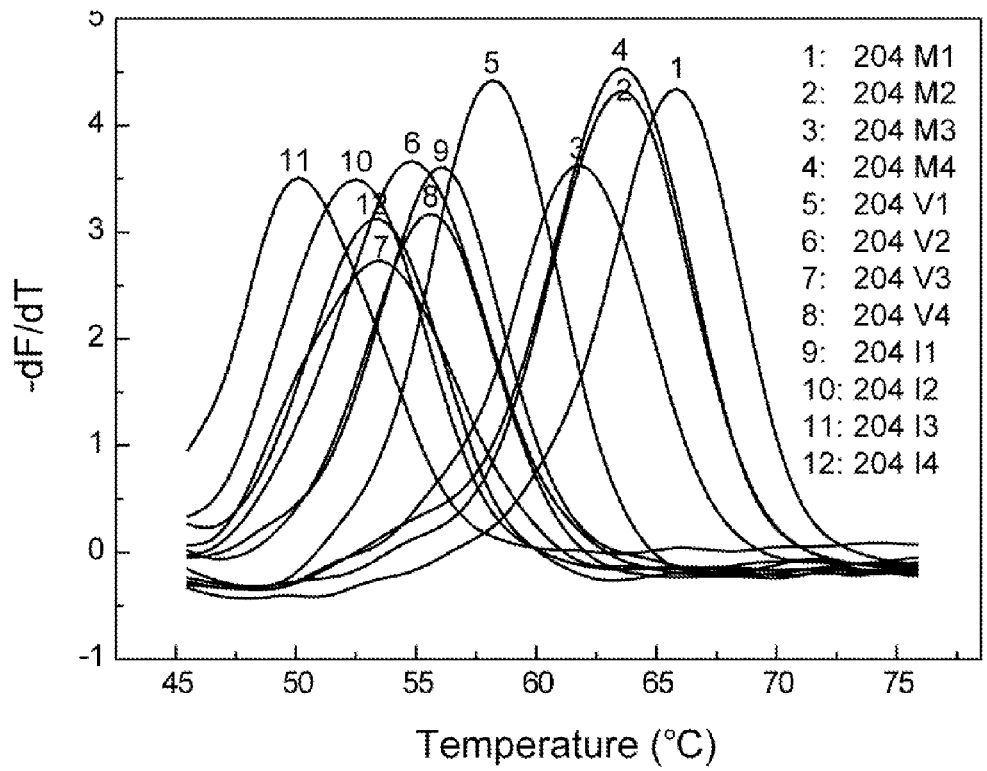

FIG. 3 shows the melting curve of an LNA modified self-quenched probe in the presence of different target sequences.

Figure 4:
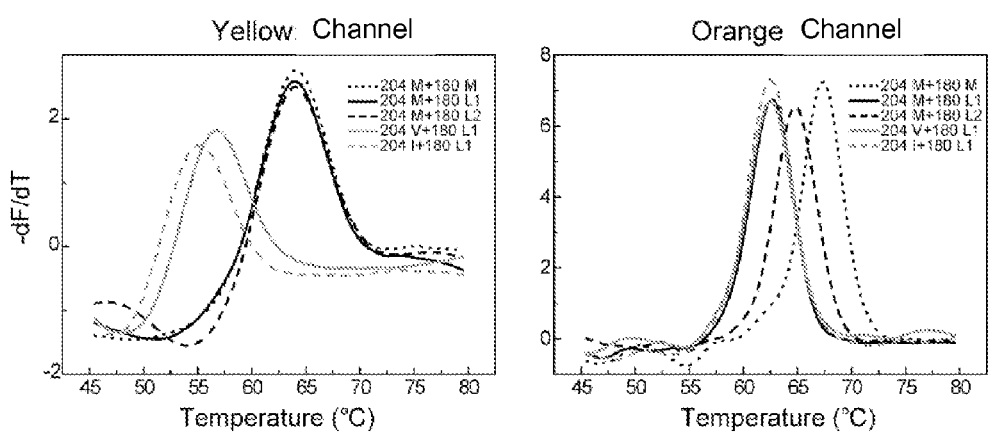

FIG. 4 shows the detection of hepatitis b virus lamivudine resistant mutations with a single tube using the method of multi-color labeled self-quenched probe melting curve. The Yellow channel detects the signals from Probe 204, the orange channel detects the signals from probe 180. In the figure, different melting curves represent a type of mutation as indicated by the icon.

Figure 5:
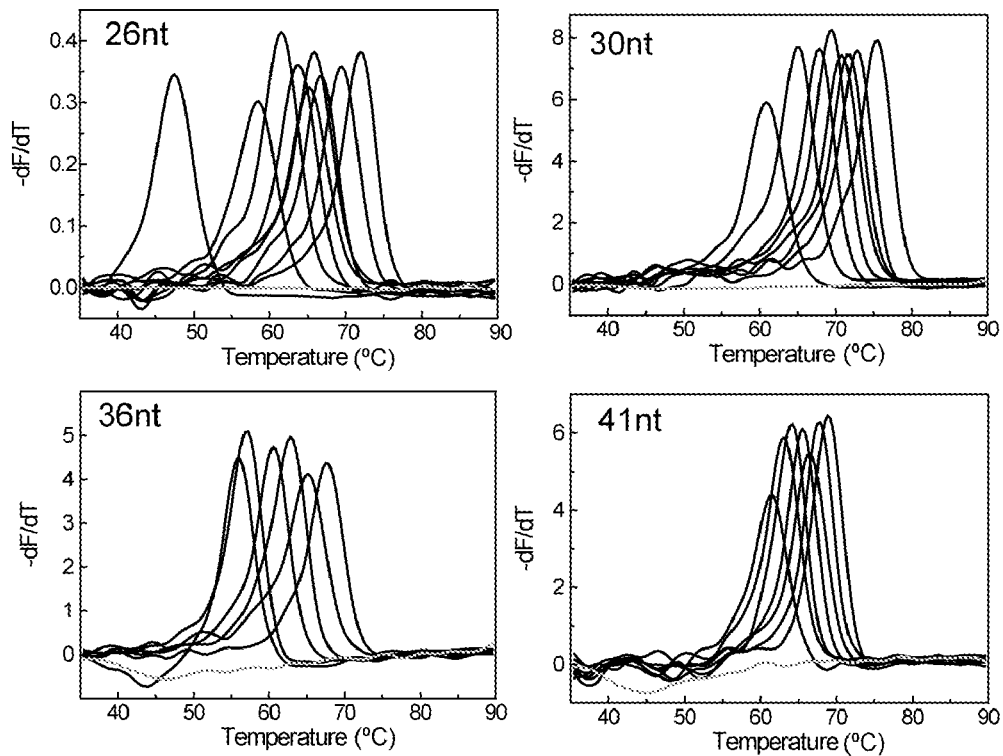

FIG. 5 shows the influence of the length of a linear self-quenched probe on the melting curve. Linear self-quenched probes with a length of 26, 30, 36, 41 nt bases are referred to as 26-nt probe, 30-nt probe, 36-nt probe, and 41-nt probe, respectively (see the 26 nt, 30 nt, 36 nt, and 41 nt panels in FIG. 5, respectively). It also shows for these probes, the results of melting curve analysis for target sequences (targets) of different extent of matching. Melting curve analysis can be carried out with all theses probes, and all the probes have the ability of differentiating target sequence variations (the specific sequence is not labeled in the figure).

Figure 6:
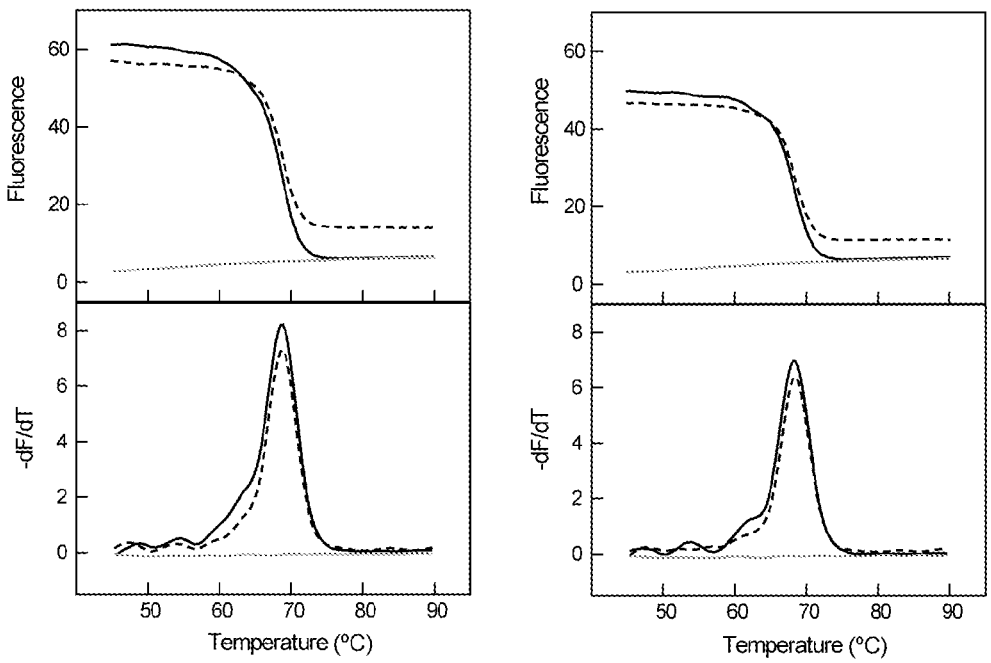

FIG. 6 shows the influence of reaction conditions on the method of PCR-melting curve analysis. With the asymmetric PCR amplification, no matter the thermophilic polymerase employed has an exonuclease activity (Taq, solid line) or a greatly reduced exonuclease activity (Taq FS, dashed line) and no matter whether a three-step method (left panel) or a two-step method (right panel) is used, it always gives a melting curve analysis result. The grey line indicates situations when a template is absent. However, whenever a symmetric PCR amplification is used, no melting curve analysis result is obtained (not shown in the figure).

Figure 7:
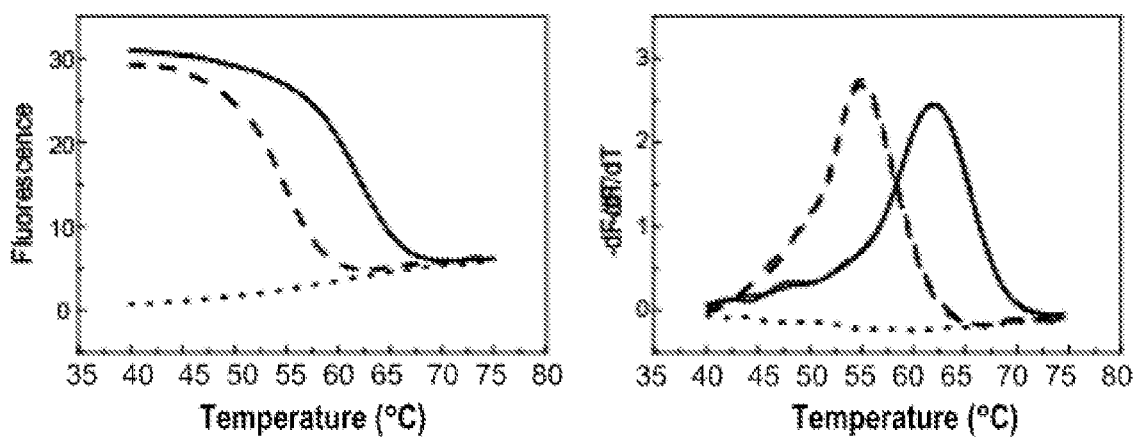

FIG. 7 shows the melting curve of a hairpin-type self-quenched probe with different target sequences. The left panel shows the corresponding denaturation curve where fluorescence intensity changes with the temperature, the right panel is obtained by making a derivation of the changes in fluorescence intensity with the change of temperature as shown in the left panel, and taking the negative value thereof (−dF/dT), namely a melting curve. A melting curve can provide the melting temperature of a hairpin-type self-quenched probe when hybridizing with different target sequences. In the figure, a solid line indicates matched target sequence, and a dashed line indicates a target sequence with a single base mismatch, the grey line indicates the absence of a target sequence.

Figure 8:
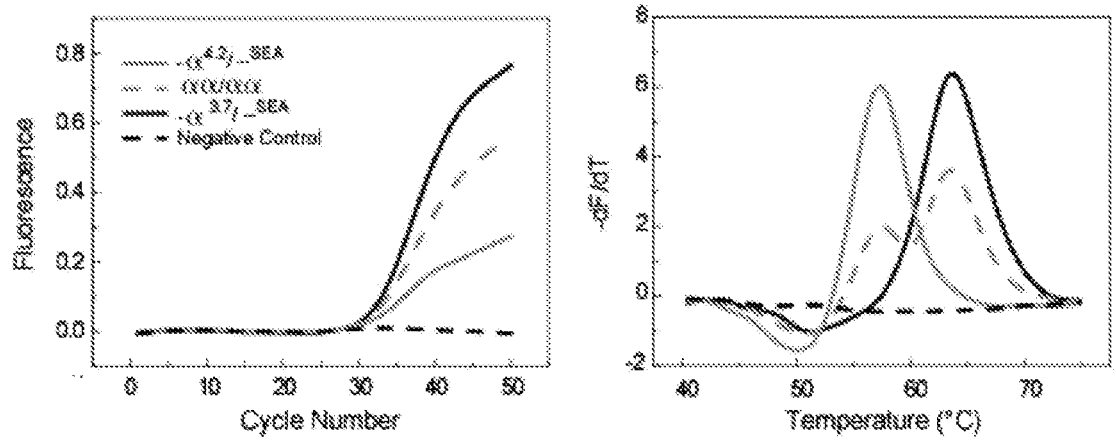

FIG. 8 shows a specimen wherein a hairpin-type self-quenched probe is used for detecting different genotypes in melting curve analysis after PCR amplification. The left panel shows the result of self-quenched probe real-time PCR detection; the right panel shows the results of melting curve analysis for a self-quenched probe after PCR. In this figure, the black solid line indicates the $-\alpha^{3.7/--SEA}$ genotype, the black dashed line indicates the negative control, the grey solid line indicates the $-\alpha^{4.2/--SEA}$ genotype, and the grey dashed line indicates the αα/αα genotype.

Figure 9:
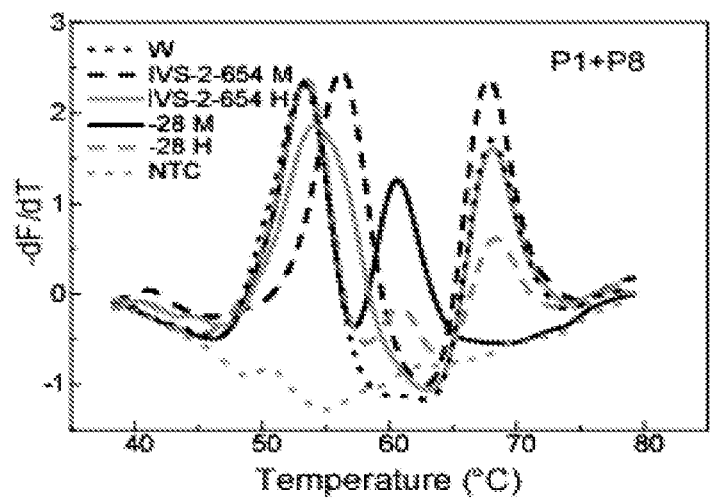

FIG. 9 shows simultaneous detection of two mutated genotypes using two probes labeled with the same fluorescent marker. The probes are designed such that the differences of their melting temperatures are enlarged, the probe with a higher melting temperature (P1) detects the mutant, and its melting temperature is higher than the wild type low melting temperature probe (P8). This way, the two would not affect each other, making it possible to detect multiple genotypes using two probes in one channel. In this figure, the genotype represented by each melting curve is indicated by the icon.

Figure 10:
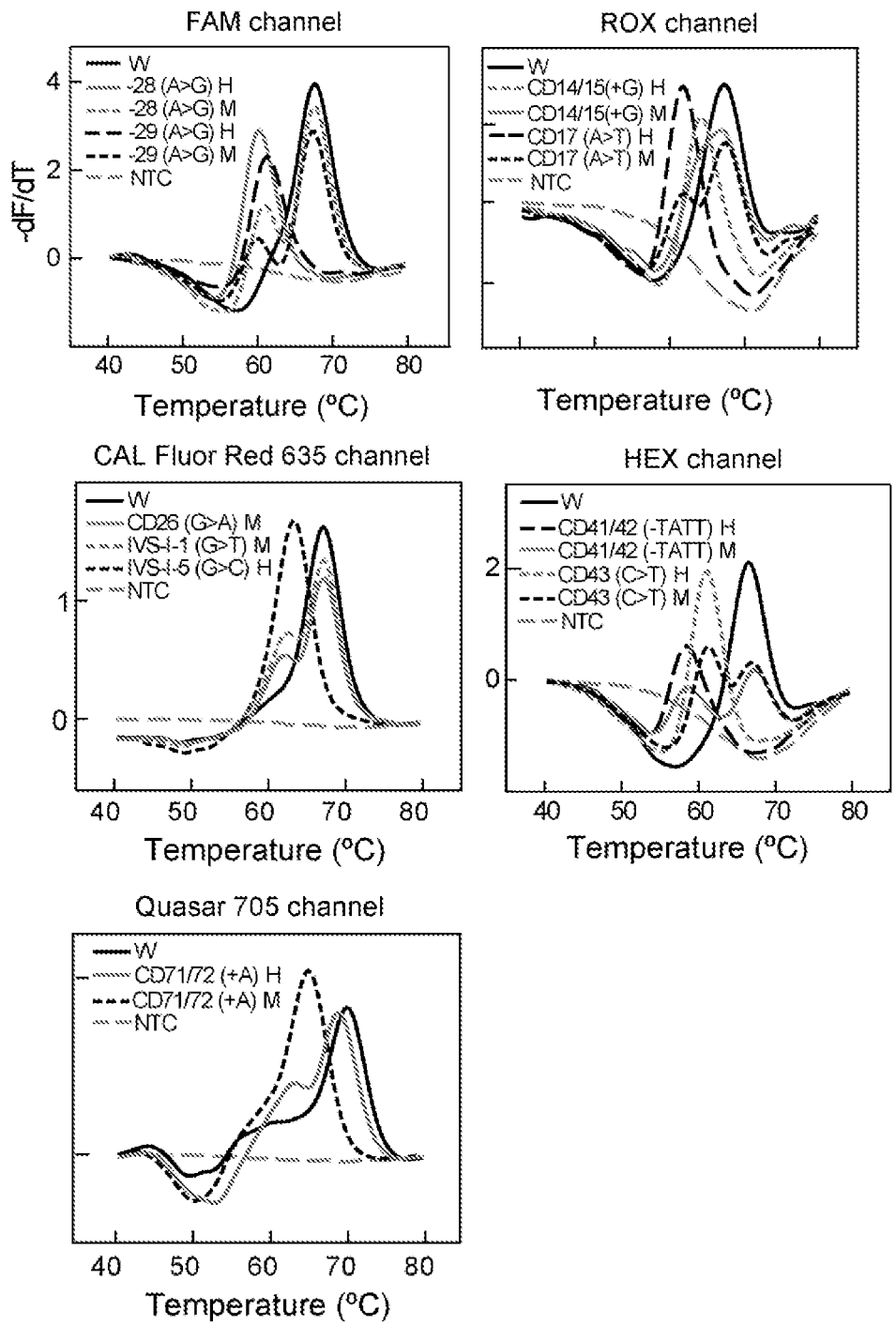

FIG. 10 shows multiple mutations in a β-globin gene detected in a single reaction tube with a mixture of five different fluorescently labeled hairpin-type self-quenched probes. This system uses five detection channels of Rotor-gene 6000, and 5 probes labeled with corresponding fluorescent substances are designed. The genotype of multiple mutated sites in the β-globin gene is detected, respectively. Each of the small panels in the figure shows the result of detection in the five fluorescence channels, the result given by each fluorescence channel corresponds to the detection result of the corresponding fluorescent probe. In the figure, the genotype represented by each melting curve is as indicated by the icon.

EXAMPLES

The following examples in combination with the figures serve to further illustrate the present invention. These examples only serve to illustrate the invention rather than demonstrating all the possibilities of the present invention, and the present invention is not limited by the material, reaction conditions, or parameters mentioned in these examples. Anyone with certain experience in the related field will be able to accomplish the detection of mutations as described in the present invention according to the principle of the present invention while using other similar materials or reaction conditions. These will not depart from the basic concepts described for the present invention.

Example 1

Artificially designing different complementary target nucleic acid sequences to examine the ability of using the method of linear self-quenched probe melting curve to detect nucleic acid sequence variations.

In this example, a self-quenched probe directed to the 5' untranslated region of the α-globin gene was designed. By artificially synthesizing target nucleic acid sequences completely complementary to the probe or with a point mutation, the ability of the method of self-quenched probe melting curve in distinguishing different target nucleic acid sequences was examined. The self-quenched probe and the target nucleic acid sequences used are:

```
Probe 1:
                                      (SEQ ID NO: 1)
5'-FAM-CCTGGTGTTTGTTCCTTCCC-BHQ-3',
the linkage between the first and the second
bases in the 5' end is a phosphorothioated
linkage.

Target 1:
                                      (SEQ ID NO: 2)
5'-GCACCGGGAAGGAACAAACACCAGGACGCA-3'

Target 2:
                                      (SEQ ID NO: 3)
5'-GCACCGGGAAGGAATAAACACCAGGACGCA-3'
``` wherein, the underlined part of the target nucleic acid sequence is complementary to the probe, the boxed part of Target 2 indicates the mutated base, the target nucleic acid sequences and the probes were all synthesized by Sangon Biotech (Shanghai) Co., LTD.

In 25 μL reaction solution, there were 2.5 μL 10×PCR buffer (without $Mg^{2+}$), 1.5 mM $MgCl_2$, 5 pmol probe 1, without the target nucleic acid sequence or with 10 pmol of one of the target nucleic acid sequences mentioned above. Melting curve analysis was performed for the above mixture. The reaction program was: 95° C. denaturation 1 min; maintaining at 40° C. for 2 min; then increasing the temperature from 40° C. to 80° C. with a rate of 1° C./step to perform the melting curve analysis, and collecting the fluorescence signal from the FAM channel. This experiment was performed in a Rotor-Gene 6000 real-time PCR machine.

The result is shown in FIG. 1, from which we could see that in the absence of a target nucleic acid sequence, the self-quenched probe was in the state of single-stranded free curling, the fluorescent group and the quenching group were close to each other, and the fluorescence emitted by the fluorescent group was quenched by the quenching group; with the change of the temperature, the change of the fluorescence intensity was not evident; in the presence of a target nucleic acid sequence, the self-quenched probe formed a rigid and stable double-stranded structure with a complementary target nucleic acid sequence at low temperature, so that the fluorescent group was apart from the quenching group and fluorescence was emitted, with the increase of the temperature, the double-stranded structure melted gradually, and the fluorescence was gradually reduced. For different target nucleic acid sequences, double-stranded structures with different stabilities were formed, which had respective different melting temperatures. Wherein the double-stranded structure formed with the self-quenched probe completely complementary to the target nucleic acid sequence (Target 1) was relatively stable, and thus having a relatively high melting temperature; the double-stranded structure formed with the mutated target nucleic acid sequence had a relatively poor stability, and thus having a relatively low melting temperature. When the target nucleic acid sequence added was Target 1, the melting temperature of the self-quenched probe was 66.97° C.; when the target nucleic acid sequence added was Target 2 (i.e. with a mismatched base), the melting temperature of the self-quenched probe was 60.98° C. Therefore, based on differences in the melting temperatures of self-quenched probes, it would be possible to determine which target nucleic acid sequence was added. Therefore, the method of self-quenched probe melting curve can be used to detect nucleic acid sequence variations.

Example 2

Detecting specimens of different genotypes using the method of linear self-quenched probe PCR-melting curve analysis.

In this example, a self-quenched probe directed to the 5' untranslated region of the α-globin gene was designed (probe 1, see example 1). The α1-globin gene was distinguished from the α2-globin gene based on the differences of probe melting temperatures; human genomic DNA was used as the template, after real-time PCR amplification, melting curve analysis was performed for Probe 1, to illustrate that the method of self-quenched probe melting curve may be used for genotyping. The primers used were:

```
P1:
                                         (SEQ ID No: 4)
5'-GCAAGCCCTCACGTAGCGAAGTAGAGGAGTCTGAATCTGGA-3'
and P2:
                                         (SEQ ID No: 5)
5'-GCAAGCCCTCACGTAGCGAATCCCTCTGGCGATAGTCA-3'.
```

The PCR reaction system was: in 25 μL reaction solution, there were 2.5 μL 10×PCR buffer (without $Mg^{2+}$), 4.0 mM $MgCl_2$, 5 pmol probe 1, 0.2 mM dNTP, 1U Hotstart Taq DNA polymerase, 0.1 μM upstream primer P1, 1 μM downstream primer P2, 0.1 μM Probe 1, 5 μL human genome template (about 50 ng) or 5 μL sterile water (negative control). There were three types of specimens: αα/αα, $-α^{3.7}/--^{SEA}$ (only with the α2-globin gene) and $-α^{4.2}/--^{SEA}$ (only with the α1-globin gene). The conditions of the PCR reaction were: 95° C. 5 min pre-denaturation; the cycles were 95° C. 15 s, 52° C. 20 s, 72° C. 20 s, 50 cycles; collecting fluorescence data from the FAM channel during the annealing stage of each cycle. After the PCR reaction, 95° C. denaturation for 1 min, maintaining at 35° C. for 2 min, then increasing the temperature from 35° C. to 80° C. with a rate of 1° C./step to perform the melting curve analysis, and collecting the fluorescence signal from the FAM channel. This experiment was performed in a Rotor-Gene 6000 real-time PCR machine.

The linear self-quenched probe (Probe 1) was completely matched to the 5' untranslated region of the α2-globin gene, while having one mismatched base with the sequence of the 5' untranslated region of the α1-globin gene. As shown in FIG. 2, when Probe 1 bound to the completely matched sequence, the melting temperature was relatively high (65.13° C.), and when it bound to the sequence with a single base difference, the melting temperature was relatively low (58.48° C.). Since the reproducibility of the fluorescence intensity of a real-time PCR amplification curve is relatively poor and since the differences of various genotypes reside in the differences of the fluorescence intensity of the amplification curves (see FIG. 2, left panel), it was difficult to distinguish different genotypes. However, the melting curve analysis (FIG. 2, right panel) after the PCR reaction could very well distinguish different genotypes. The genotype αα/αα comprised the α1-globin gene and the α2-globin gene, thereby having two melting peaks; the genotype $-α^{3.7}/--^{SEA}$ only comprised the α2-globin gene, and thus only had the peak of high melting temperature; the genotype $-α^{4.2}/--^{SEA}$ only comprised the α1-globin gene, and thus only had the peak of the low melting temperature. Therefore, the method of self-quenched probe melting curve can be used for genotyping; different genotypes can be distinguished based on the presence and absence of a melting temperature peak and the value of the melting temperature.

Example 3

The ability of the method of self-quenched probe melting curve with different artificially synthesized complementary sequences to detect nucleic acid sequence variations.

The codon at position 204 in the C region of the coding region of the DNA polymerase from hepatitis B virus was mutated from methionine (M) into valine (V) (ATG→ATT) or isoleucine (I) (ATG→GTG) will result in resistance to the first-line drug lamivudine, and may be accompanied by a mutation of the codon at position 180 from leucine (L) into methionine (M) (CTG/TTG→ATG).

In this example, a self-quenched probe covering the C region of the coding region of the DNA polymerase from hepatitis B virus was designed, and artificially synthesized target nucleic acid sequences were used to examine the ability of the method using LNA modified self-quenched probe melting curve to detect nucleic acid sequence variations. The self-quenched probes and the target nucleic acid sequences used were:

```
Probe 204:
                                         (SEQ ID No. 6)
5'-TET-TTCAGTTATATGGATGATGTGG-BHQ-3'

204 W1:
                                         (SEQ ID No. 7)
5'-CAAAACCACATCATCCATATAACTGAAAGCCAAA-3'

204 W2:
                                         (SEQ ID No. 8)
5'-CAAAACCACATCATCCATATAACTAAAAGCCAAA-3'

204 W3:
                                         (SEQ ID No. 9)
5'-CAAAACCACATCATCCATATAGCTGAAAGCCAAA-3'

204 W4:
                                         (SEQ ID No. 10)
5'-CAAAAACACATCATCCATATAACTGAAAGCCAAA-3'

204 V1:
                                         (SEQ ID No. 11)
5'-CAAAACCACATCATCCACATAACTGAAAGCCAAA-3'

204 V2:
                                         (SEQ ID No. 12)
5'-CAAAACCACATCATCCACATAACTAAAAGCCAAA-3'
```

-continued

```
204 V3:
                                            (SEQ ID No. 13)
5'-CAAAACCACATCATCCACATAGCTGAAAGCCAAA-3'

204 V4:
                                            (SEQ ID No. 14)
5'-CAAAAACACATCATCCACATAACTGAAAGCCAAA-3'

204 I1:
                                            (SEQ ID No. 15)
5'-CAAAACCACATCATCAATATAACTGAAAGCCAAA-3'

204 I2:
                                            (SEQ ID No. 16)
5'-CAAAACCACATCATCAATATAACTAAAAGCCAAA-3'

204 I3:
                                            (SEQ ID No. 17)
5'-CAAAACCACATCATCAATATAGCTGAAAGCCAAA-3'

204 I4:
                                            (SEQ ID No. 18)
5'-CAAAAACACATCATCAATATAACTGAAAGCCAA-3'
```

Wherein, the boxed bases in the probe were replaced with the corresponding locked nucleic acids (LNA), and the linkage between the first base and the second base in the 5' end was a phosphorothioated linkage; the underlined part of the target nucleic acid sequence is complementary to the probe, the bold bases in the TARGET NUCLEIC ACID SEQUENCE and the bases in the probe were unmatched, wherein 204 M1, 204 M2, 204 M1, 204 M3, and 204 M4 are wild type target nucleic acid sequences having different polymorphisms; 204 V1, 204 V2, 204 V3, and 204 V4 are target nucleic acid sequences with the amino acid at position 204 (which has different polymorphisms) changed from methionine into valine; 204 I1, 204 I2, 204 I3, and 204 I4 are target nucleic acid sequences with the amino acid at position 204 (which has different polymorphisms) changed from methionine into isoleucine.

The target nucleic acid sequences and probes were all synthesized in Shanghai Sheng Gong biological engineering Co., LTD.

In 25 μL reaction solution, there were 2.5 μL 10×PCR buffer (with 25 mM $Mg^{2+}$), 0.2 μM probe, 0.4 μM target nucleic acid sequence. Melting curve analysis was performed for the above mixture, the reaction program was: 95° C. denaturation for 1 min, maintaining at 40° C. for 2 min, then increasing the temperature from 45° C. to 76° C. with a rate of 1° C./step to perform the melting curve analysis, and collecting the fluorescence signal from the Yellow channel. This experiment was performed in a Rotor-Gene 6000 real-time PCR machine.

The results are shown in FIG. 3, from which we could see that, when different target nucleic acid sequences were added, the probe would have a respectively different melting temperature. When the target nucleic acid sequence was the wild type target nucleic acid sequence 204 W1, 204 W2, 204 W3, and 204 W4, the melting temperature of the probe was respectively 65.88° C., 63.88° C., 63.54° C. and 61.79° C.; when the target nucleic acid sequence was the target nucleic acid sequences 204 V1, 204 V2, 204 V3, 204 V4, 204 I1, 204 I2, 204 I3, and 204 I4a comprising a mutation, the melting temperature of the probe was respectively 58.23° C., 54.8° C., 53.42° C., 55.62° C., 56.07° C., 52.46° C., 50.1° C. and 52.53° C. Although few melting temperatures were close to each other, the differences between the melting temperatures of the 4 wild types and the 8 mutants were relatively big, even for the wild type (204 W3) and the mutant (204 V1) having the smallest differences, the difference between their melting temperatures was 3.56° C. Thus, the method using LNA modified self-quenched probe melting curve can be used to detect nucleic acid sequence variations.

Example 4

Simultaneous detection of mutations at multiple different sites in a single tube with multi-color labeled linear self-quenched probes.

As indicated by the aforementioned examples, one self-quenched probe may cover adjacent mutation sites simultaneously and detect multiple mutations simultaneously. This example shows that even for mutations that are not adjacent to each other, multiple detection in a single tube can still be realized using self-quenched probes labeled with different colors.

In this example, self-quenched probes respectively directed to the B and C regions of the coding region of the DNA polymerase from hepatitis B virus were designed, and each probe was labeled with a different fluorescent group. The probes used were Probe 204 and Probe 180, and the primers used were F and R, the sequences of the primers and the probes are:

Probe 204 (the same as in Example 3),

```
Probe180:
                                            (SEQ ID No. 19)
5'-ROX-CCGTTTCTCATGGCTCAGTTTACTAG-BHQ-3', F:
                                            (SEQ ID No. 20)
5'-GGAAACTGCACTTGTATTCCCATCCCATC-3', R:
                                            (SEQ ID No. 21)
5'-GTTTACAGGAAGTTTCCTAAAACAC-3'.
```

Wherein in the probe, the boxed bases were replaced by a corresponding LNA, and the linkage between the first and the second bases in the 5' end was a phosphorothioated linkage.

The PCR reaction system was: in a 25 μL reaction solution, there were 2.5 μL 10×PCR buffer (without $Mg^{2+}$), 4.0 mM $MgCl_2$, 0.2 mM dNTP, 1 U Hotstart Taq DNA polymerase, 0.1 μM upstream primer F, 1 μM downstream primer R, 0.2 μM probe, 5 μL artificially constructed plasmid template or sterile water (negative control). The types of plasmid templates used includes: 204M+180M; 204M+180L1; 204M+180L2; 204V+180L1; 204 I+180L1. Wherein the template 204 M+180M means that the amino acid encoded by the codon at position 204 in the C region of the template is methionine, and the amino acid encoded by the codon at position 180 in the B region is methionine; 204M+180L means that the amino acid encoded by the codon at position 204 in the C region of the template is methionine, and the amino acid encoded by the codon at position 180 in the B region is leucine; 204M+180L2 means that the amino acid encoded by the codon at position 204 in the C region of the template is methionine, and the amino acid encoded by the codon (which is CTG) at position 180 in the B region is leucine; 204V+180L1 means that the amino acid encoded by the codon at position 204 in the C region of the template is valine, and the amino acid encoded by the codon (which is TTG) at position 180 in the B region is leucine; 204 I+180L1 means that the amino acid encoded by the codon at position 204 in the C region of the template is isoleucine, and the amino acid encoded by the codon (which is TTG) at position 180 in the B region is leucine.

The conditions of the PCR reaction were: 95° C. 3 min pre-denaturation; the cycles were 95° C. 15 s, 50° C. 20 s, 72° C. 20 s, 40 cycles; fluorescence data were collected from the Yellow and Orange channels in the annealing stage of each cycle. After the PCR reaction, at 95° C. denatured for 1 min, maintaining at 40° C. for 2 min; then increasing the temperature from 45° C. to 80° C. with a rate of 1° C./step to perform the melting curve analysis, and collecting the fluorescence signal from the Yellow and Orange channels. This experiment was performed in a Rotor-Gene 6000 real-time PCR machine.

The results are shown in FIG. 4, Probe 204 (Yellow channel) and Probe 180 (Orange channel) can both differentiate the genotypes of the templates according to their melting temperatures. When placed in a single tube, multiple self-quenched probes labeled with different colors do not result in interferences between different probes. Each probe could very well detect the mutation in the respective region that it covers. Thus, by labeling self-quenched probes with multiple colors, mutations at multiple different sites can be detected simultaneously.

Example 5

Examining the Influence of the Length of a Linear Self-Quenched Probe on the Melting Curve Analysis We have designed linear self-quenched probes with a length of 26, 30, 36, and 41 bases, respectively, which were referred to as 26-nt probe, 30-nt probe, 36-nt probe, and 41-nt probe, respectively (see table 1). Their influence on the melting curve analysis of target sequences (targets) with different matching degrees were examined. The reaction conditions were: in a 25 μL reaction solution, there were 2.5 μL 10×PCR buffer [10 mM Tris-HCl, 50 mM KCl, 5% glycerol (W/V), pH 8.6], 3.0 mM MgCl$_2$, 0.2 μM probe, without the target nucleic acid sequence or with one of the above target nucleic acid sequences added to a final concentration of 0.4 μM. Melting curve analysis was performed for the above mixture, the reaction program was: 95° C., denaturation for 1 min; maintaining at 35° C. for 5 min, then increasing the temperature from 35° C. to 90° C. with a rate of 1° C./step to perform the melting curve analysis.

The results (see FIG. 5) indicated that all of these linear self-quenched probes with a length of 26, 30, 36, or 41 bases can be used to perform melting curve analysis, and all of them had the ability of differentiating target sequence variations.

TABLE 1

Linear self-quenched probes of four different lengths and the target sequences thereof

| Probes/targets | Sequences |
|---|---|
| 26-nt probe | 5'-ROX-CCTGATACCGACGAGCAAGCACTGGA-BHQ-3' (SEQ ID No. 22) |
| target 1 | 5'-ATTTCCAGTGCTTGCTCGCCGGTATCAGGCTG-3' (SEQ ID No. 23) |
| target 2 | 5'-ATTTCCAGTGCTTGCTCGCCGGTATCTGGCTG-3' (SEQ ID No. 24) |
| target 3 | 5'-ATTTCCAGCGCTTGCTCGCCGGTATCAGGCTG-3' (SEQ ID No. 25) |
| target 4 | 5'-ATTTCCAGTGCTTGCTCGCCAGTATCAGGCTG-3' (SEQ ID No. 26) |
| target 5 | 5'-ATTTCTAGTGCTTGCTCGCCGGTATCTGGCTG-3' (SEQ ID No. 27) |
| target 6 | 5'-ATTTCCAGCGCTTGCTCGCCGGTATCTGGCTG-3' (SEQ ID No. 28) |
| target 7 | 5'-ATTTCCAGCGCTTGTTCGCCGGTATCAGGCTG-3' (SEQ ID No. 29) |
| target 8 | 5'-ATTTCTAGCGCTTGCTCGCCGGTATCTGGCTG-3' (SEQ ID No. 30) |
| target 9 | 5'-ATTTCCAGCGCTTGTTCACCTGTATCAGGTTG-3' (SEQ ID No. 31) |
| 30-nt probe | 5'-ROX-CACTGGAAATTTGTGATGCATTGGCTCGCT-BHQ-3' (SEQ ID No. 32) |
| target 1 | 5'-AACGACAATCACATCTACCGCACCAGAGCGAGCCAATGCATCACAAATTTCCAGTGC-3' (SEQ ID No. 33) |
| target 2 | 5'-AACAACAATCACATCTACCGCACCAGAGCGAGCCAGTGCATCACAAATTTCCAGTGC-3' (SEQ ID No. 34) |
| target 3 | 5'-AACGACGATGACATCTACCGCACCAGAGCGAGCCAGTGCATCACAAATTTCCAGCGC-3' (SEQ ID No. 35) |
| target 4 | 5'-AACAACAATCACATCTACCGCACCAGAGCGAGCCAATGCATCACAAATCTCCAGTGC-3' (SEQ ID No. 36) |
| target 5 | 5'-AACAACAATCACATCTACCGCACCAGAACGAGCCAGTGCATCACAAATTTCCAGTGC-3' (SEQ ID No. 37) |
| target 6 | 5'-AACAACAATCACATCTACTGCACCAGAGCGAGCTAGTGCATCACAAATTTCCAGCGC-3' (SEQ ID No. 38) |
| target 7 | 5'-AACAACAATCACATCTACCGCACCAGAGCGAGCCAGCGCATCACAGATTTCCAGCGC-3' (SEQ ID No. 39) |
| target 8 | 5'-AACGACGATGACATCTACCGCACCAGAGCGAGCCAGCGCATCACAGATTTCTAGCGC-3' (SEQ ID No. 40) |
| 36-nt probe | 5'-TET-ATTAAGCAGATGCGTTTTCCCGGTTACTTCTTGATC-BHQ-3' (SEQ ID No. 41) |
| target 1 | 5'-AACTCCATCACGATCAAGAAGTAACCGGGAAAACCCATCTGGTTTATCACATCGAGCTC-3' (SEQ ID No. 42) |
| target 2 | 5'-AACTCCATCACGATCAAGAAGTAACCGGGAAAGCCCATCTGGTTAATCACATCGAGCTC-3' (SEQ ID No. 43) |
| target 3 | 5'-AACTCCATCACGATCAAGAAGTAGCCGGGAAAGCCCATCTGGTTAATCACATCGAGCTC-3' (SEQ ID No. 44) |
| target 4 | 5'-AACTCCATCACGATCAAGAAGTATCCGGGAAAGCCCATCTGGTTAATCACATCGAGCTC-3' (SEQ ID No. 45) |

TABLE 1-continued

Linear self-quenched probes of four different
lengths and the target sequences thereof

| Probes/targets | Sequences |
|---|---|
| target 5 | 5'-AACTCCATCACGACCAAGAAGTATCCGGGAAAGCCCATCTGGTTAATCACATCGAGCTC-3' (SEQ ID No. 46) |
| target 6 | 5'-AATTCCATCACGATCAAGAAATAGCCGGGAAAGCCCATCTGGTTGATGACATCGAGCTC-3' (SEQ ID No. 47) |
| 41-nt probe | 5'-ROX-TGTGATTAACCAGGCTTTCCCGATTACTTCTTGATCGTGAT-BHQ-3' (SEQ ID No. 48) |
| target 1 | 5'-AACTCCATCACGATCAAGAAGTAACCGGGAAAGCCCATCTGGTTAATCACATCGAGCTC-3' (SEQ ID No. 49) |
| target 2 | 5'-AACTCCATCACGATCAAGAAGTATCCGGGAAAGCCCATCTGGTTAATCACATCGAGCTC-3' (SEQ ID No. 50) |
| target 3 | 5'-AACTCCATCACGATCAAGAAGTAGCCGGGAAAGCCCATCTGGTTAATTACATCGAGCTC-3' (SEQ ID No. 51) |
| target 4 | 5'-AACTCCATTACGATCAAGAAGTATCCGGGAAAGCCCATCTGGTTAATCACATCGAGCTC-3' (SEQ ID No. 52) |
| target 5 | 5'-AACTCCATCACGACCAAGAAGTATCCGGGAAAGCCCATCTGGTTAATCACATCGAGCTC-3' (SEQ ID No. 53) |
| target 6 | 5'-AACTCCATCACGATCAAGAAGTAACCGGGAAAACCCATCTGGTTTATCACATCGAGCTC-3' (SEQ ID No. 54) |
| target 7 | 5'-AATTCCATCACGATCAAGAAATAGCCGGGAAAGCCCATCTGGTTGATGACATCGAGCTC-3' (SEQ ID No. 55) |

Example 6

The Influence of Reaction Conditions on the Method of PCR-Melting Curve Analysis We compared the symmetric PCR and the asymmetric PCR respectively, using the Taq enzyme having the exonuclease activity and the TaqFS enzyme having reduced exonuclease activity. The PCR amplification cycles may use a two-step method or a three-step method, the experimental conditions were: the PCR amplification system was: in a 25 µL reaction system, there were 1×PCR buffer (10 mM Tris-HCl, 50 mM KCl, 5% glycerol, pH 8.6), 3.0 mM MgCl$_2$, 200 µM dNTPs, 1.0 U Taq or TaqFS, 0.04 µM upstream primer, 0.4 µM downstream primer, 0.1 µM probe, 5 µL plasmid template (1.0×10$^5$ copies), water as the negative control. The PCR amplification program was: 95° C. 3 min pre-denaturation, then 95° C. 10 s, 68° C. (lowered by 1 degree in each cycle) 10 s, 72° C. 20 s, 10 cycles; then at 95° C. for 10 s, 58° C. 10 s, 75° C. (three-step method) or 58° C. (two-step method) 20 s, for 40 cycles. The fluorescence signal from the ROX channel was collected in the annealing stage of each cycle. After the PCR reaction, melting curve analysis was performed, and the program of the melting curve analysis was: 95° C. denaturation for 1 min, maintaining at 45° C. for 5 min, then increasing the temperature from 45° C. to 90° C. with a rate of 1° C./step to perform the melting curve analysis.

The amplified fragment was a fragment of the recA gene of vibrio cholerae, the upstream primer is:

(SEQ ID No. 56)
5'-TGTGCGTTTATCGATGCCGAGCAC-3', and the downstream primer is:

(SEQ ID No. 57)
5'-GCTTTTGGTGTCAAAGCCGC-3, the linear self-quenched probe is:

(SEQ ID No. 58)
5'-ROX-CCTGATACCGACGAGCAAGCACTGGA-BHQ2-3'.

The results of the experiment are shown in FIG. 6. It can be seen that no melting curve analysis results were obtained whenever the symmetric PCR amplification was used (not shown), However, ith the asymmetric PCR amplification, no matter the thermostable DNA polymerase employed has an exonuclease activity (Taq) or a greatly reduced exonuclease activity (TaqFS) and no matter a three-step method or a two-step method was used, it always gave a melting curve analysis result. Although when Taq was used, the degree of enzyme digestion was bigger, it essentially did not affect the result of the experiment.

Example 7

Examining the ability of the method of hairpin type self-quenched probe melting curve to detect target sequence variations with artificially synthesized complementary target sequences.

In this example, a hairpin type self-quenched probe directed to the 5' untranslated region of the α-globin gene was designed, By artificially synthesizing target nucleic acid sequences completely complementary to the probe or with a point mutation, the ability of the method of hairpin type self-quenched probe melting curve in distinguishing different target nucleic acid sequences was examined. The self-quenched probe used was Probe H: 5'-FAM-cgGGTGTTTGTTCCTTCCCG-BHQ1-3' (SEQ ID No. 59), the underline indicates the arm sequence of the hairpin, letters in lower case indicates the artificially added sequences unrelated to the target sequence. The completely complementary target sequence was Target-M: 5'-AC CGGGAAGGAACAAACACCAGGACGCAAAAA GCA-CGGGGCTGGGCTG-3' (SEQ ID No. 60);

The target sequence comprising a mutation was Target-UM:

(SEQ ID No. 61)

5'-ACCGGGAAGGAA[T]AAACACCAGGACGCAAAAAGCA-CGGGGCTGGGCTG-3';

the underlined part was complementary to the probe, and the boxed letter indicates that the position of the corresponding base mutation.

The melting curve analysis system of the artificially synthesized target sequence and the fluorescent probe was: in a 25 µL reaction solution, there were 1×SSP buffer [67 mM Tris-HCl pH 8.0, 16.6 mM (NH$_4$)$_2$SO$_4$, 6.7 mM EDTA, 0.085 mg/mL BSA], 2.0 mM MgCl$_2$, 0.1 μM hairpin type self-quenched probe, 0.2 μM target sequence (Target-M or Target-UM) or without the target sequence (negative control). The program of melting curve analysis was: 95° C. denaturation for 1 min; maintaining at 35° C. for 2 min; then increasing the temperature from 40° C. to 75° C. with a rate of 1° C./step to perform the melting curve analysis, and collecting the fluorescence signal from the FAM channel during the melting curve analysis. This experiment was performed in a Rotor-Gene 6000 real-time PCR machine (Corbett Research, Australia).

As shown in FIG. 7 (left panel), in the absence of the target sequence, during the change of the temperature from low temperature to high, the stem-loop structure of the hairpin type self-quenched probe opened gradually, the fluorescence signal detected increases with the increase of the temperature; wherein the point with the biggest change of fluorescence corresponds to the temperature that is the melting temperature of the secondary structure of the hairpin type self-quenched probe. In the presence of a complementary target sequence, the hairpin type self-quenched probe emitted strong fluorescence at low temperature; with the increase of the temperature, the fluorescence intensity decreased gradually, when it was close to the melting temperature of the double-stranded hybrid formed between a probe and a target, the speed at which the fluorescence intensity decreased was faster, wherein the temperature with the biggest change of fluorescence corresponds to the temperature that is the melting temperature of the double-stranded hybrid formed between a probe and the target sequence; when the temperature was relatively high, the fluorescence intensity did not continue to change any more. The stability of the double-stranded hybrid formed between the hairpin type self-quenched probe and different target sequences were different, and thereby having different Tm values, differences of target sequences can be determined from the difference of the Tm values. As shown in FIG. 7 (right panel) the orientation of the melting peak of the secondary structure of a hairpin type self-quenched probe is different from that of a double-stranded hybrid, and they would not interfere with each other at all. In addition, comparing to the melting peak of the double-stranded hybrid, the peak of the secondary structure of the probe is negligible. Thus, hairpin type self-quenched probe can also be used for melting curve analysis.

Example 8

Detecting Specimens of Different Genotypes Using PCR-Melting Curve Analysis with Hairpin Type Self-Quenched Probes Using the hairpin type self-quenched probe H in Example 7 and the reaction system and reaction conditions in Example 2 (replace Probe 1 with Probe H). The results are shown in FIG. 8. Since the reproducibility of the fluorescence intensity of a real-time PCR amplification curve is relatively poor, while the differences of various genotypes reside in the differences of the fluorescence intensity of the amplification curves (FIG. 8 left panel), it was difficult to distinguish different genotypes by real-time PCR curves. However, the melting curve analysis (FIG. 8, right panel) after the PCR reaction could very well distinguish different genotypes. The genotype αα/αα comprised the α1-globin gene and the α2-globin gene, thereby having two melting peaks; the genotype $-\alpha^{3.7}/--^{SEA}$ only comprised the α2-globin gene, and thus only had the peak of high melting temperature; the genotype $-\alpha^{4.2}/--^{SEA}$ only comprised the α1-globin gene, and thus only had the peak of the low melting temperature. Therefore, the method of self-quenched probe melting curve can be used for genotyping, different genotypes can be distinguished based on the presence or the absence of a melting peak and the value of the melting temperature.

Comparing the PCR-melting curve analysis results of linear self-quenched probes and hairpin type self-quenched probes, it can be seen that in low temperature regions, the background signal of the hairpin type self-quenched probe is low, while the linear self-quenched probe has an obvious noise peak in the low temperature region, this result demonstrated the advantage of the hairpin type self-quenched probe.

Example 9

Simultaneous Detection of the Genotype of Two Mutations Using Two Probes Labeled with the Same Fluorescence For mutations that are co-existing but are relatively far apart from each other, it would be necessary to use different probes to detect them; by using different probes labeled with the same fluorescence while having different melting temperatures, it was also possible to detect mutations of different regions in a single reaction tube. Taking the detection of the two mutations −28(A>G) and IVS-2-654(C>T) in β-globin as an example.

We have designed two probes directed to the wild type of said two mutations, the difference of their Tm values was relatively big. Thus, when the two probes hybridized with the target, their melting peaks were relatively far from each other and it was easy to differentiate of the two melting curves derived from the two different probes. When the template comprised a mutation, a new melting peak would appear, depending on the Tm value of this newly appeared melting peak, it was possible to differentiate the mutations in different regions. The self-quenched hairpin probe P1 is completely matched to the wild type target, and thereby having a relatively low Tm value when hybridized to the −28(A>G) mutated target; the self-quenched hairpin probe P8 is completely matched to the IVS-2-654(C>T) mutated target, and thereby having a relatively low Tm value when hybridized to the wild type target. The PCR amplification system was: in a 25 μL reaction system, there were 1×SSP buffer [67 mM Tris-HCl, pH 8.0, 16.6 mM (NH$_4$)$_2$SO$_4$, 6.7 mM EDTA, 0.085 mg/mL BSA], 2.0 mM MgCl$_2$, 0.2 mM dNTPs, 1 U Taq (HS) [Takara Biotechnology (Dalian) Co., Ltd, a Hotstart Taq enzyme, with the 5'→3' exonuclease activity], 0.1 μM F1, 0.8 μM primer R1, 0.05 μM primer F3, 0.4 μM primer R3, 0.2 μM probe P1, 0.15 μM probe P8 (for the sequences of each primer and probe, see table 2), 5 μL of the plasmid template or human genome DNA template (about 50 ng). The PCR amplification program was: 95° C. 5 min pre-denaturation; the cycle was: 95° C. 15 s, 52° C. 20 s, 72° C. 20 s, 50 cycles; fluorescence signals from the corresponding detection channels were collected during the annealing stage of each cycle. After the PCR reaction, melting curve analysis was performed, the program of the melting curve analysis was: 95° C. denaturation for 1 min; maintaining at 35° C. for 2 min; then increasing the temperature from 40° C. to 80° C. with a rate of 1° C./step to perform the melting curve analysis, and collecting the fluorescence signal from the corresponding detection channel. Real time PCR and the melting curve analysis were performed in a Rotor-Gene 6000 real-time PCR machine.

The results were shown in FIG. 9. When the template was wild type (W), probe P1 and P8 only had one melting temperature, respectively. The Tm value of the double-stranded hybrid formed between P1 and the wild type target was 67.92° C., the Tm value of the double-stranded hybrid formed between P8 and the wild type target was 53.27° C.; when the template was a IVS-2-654(C>T) homozygous mutant (IVS-2-654 M), the Tm value of the P8 probe was changed to 56.6° C., but the target of the P1 probe was still wild type, and the Tm value did not change; when the template was a −28(A>G) homozygous mutant (−28 M), the Tm value of the P1 probe was changed to 60.97° C., but the target of the P8 probe was still wild type, and the Tm value did not change. Thus, based on the changes of the melting temperature of each probe, we could recognize mutations of different regions, and thereby being able to detect mutations of different regions using different probes labeled with the same fluorescence.

Example 10

Simultaneous Detecting the Genotype of Multiple Mutations with Hairpin Type Self-Quenched Probes Labeled with Different Fluorescence Using self-quenched probes labeled with different fluorescence, multiple mutations can be detected in a single tube. This example describes that in the same reaction tube, multiple mutations in β-globin were detected using hairpin type self-quenched probes labeled with five different fluorescence, namely: FAM labeled probeP1 to detect the mutations −28 (A>G) and −29(A>G); ROX labeled P2 to detect the mutations CD17(A>T), CD15/16(+G), and CD14/15(+G); CAL Fluor Red 635 labeled P3 to detect the mutations IVS-1-1 (G>T), IVS-1-5(G>C), and CD26(G>A); HEX labeled P4 to detect the mutations CD41/42(−TCTT) and CD43(G>T); Quasar 705 labeled P5 to detect the mutations CD71/72(+A) and CD71/72(+T). The five probes and two pairs of primers (i.e. F1, R1, F2 and R2) were mixed (see table 2 for detailed information the primers and probes), simultaneous detection of the genotype of all these mutations could be achieved in a single tube. The PCR amplification system was: in 25 μL reaction solution, there were 1×SSP buffer, 3.0 mM MgCl$_2$, 0.2 mM dNTPs, 1 U Taq (HS), 0.1 μM F1, 1.0 μM R1, 0.2 μM F2, 1.6 μM R2, 0.2 μM P1, 0.2 μM P2, 0.1 μM P3, 0.3 μM P4, 0.1 μM P5, 5 μL human genome DNA template (about 50 ng). The PCR amplification program and the melting curve analysis program were identical to those in Example 9.

FIG. 10 provides representative test results; the genotype of the mutation covered by each probe was correctly detected.

TABLE 2

List of the primers and probes used in Example 9 and Example 10

| name | sequence* |
|---|---|
| F1 | 5'-GCAAGCCCTCACGTAGCGAACAATCTACTCCCAGGAGCA-3' (SEQ ID NO. 62) |
| R1 | 5'-GCAAGCCCTCACGTAGCGAAGCCCAGTTTCTATTGGTCTC-3' (SEQ ID NO. 63) |
| F2 | 5'-GCAAGCCCTCACGTAGCGAACCTTAGGCTGCTGGTGGTCT-3' (SEQ ID NO. 64) |
| R2 | 5'-GCAAGCCCTCACGTAGCGAAGTGCCCTTGAGGTTGTCCA-3' (SEQ ID NO. 65) |
| F3 | 5'-GCAAGCCCTCACGTAGCGAA CATCATGCCTCTTTGCACCA-3' (SEQ ID NO. 66) |
| R3 | 5'-GCAAGCCCTCACGTAGCGAAGCAATATGAAACCTCTTACATCAG-3' (SEQ ID NO. 67) |
| P1 | 5'-FAM-cGGCTGGGCATAAA AGTCAGGGCcg-Dabcyl-3' (SEQ ID NO. 68) |
| P2 | 5'-ROX- cacgttCCTGTGGGGCAAGGTGAACGTG-Dabcyl-3' (SEQ ID NO. 69) |
| P3 | 5'-CAL Fluor Red 635 -cGGTGAGGCCCTTGGCAGGTTGGTATCAccc-BHQ2-3' (SEQ ID NO. 70) |
| P4 | 5'-HEX-cgatccAGGTTCTTTGAGTCCTTTGGGGATCg-BHQ1-3' (SEQ ID NO. 71) |
| P5 | 5'-Quasar 705-cCTCGGTGCCTTTAGTGATGGCCga-BHQ1-3' (SEQ ID NO. 72) |
| P8 | 5'-FAM-CTGGGTTAAGGTAATAGCAATACCCA-DABCYL-3' (SEQ ID NO. 73) |

*The underline indicates sequences complementary to the target sequences, letters in lower case are added sequences unrelated to the target sequence.

REFERENCES

1. US Patent, US 2006/0019253 A1.
2. US Patent, US 2003/0224434 A1.
3. U.S. Pat. No. 7,160,998 B2.
4. U.S. Pat. No. 6,472,156 B1.
5. U.S. Pat. No. 6,140,054.
6. U.S. Pat. No. 6,635,427 B2.
7. US Patent, US 2008/0311579 A1.
8. US Patent, US 2007/0020665 A1.
9. U.S. Pat. No. 7,179,589 B2.
10. Wittwer C. T., et al, BioTechniques, 1997, 22:130-138.
11. Ririe K. M., et al, Anal. Biochem, 1997, 245:154-160.
12. Wittwer C T, et al, Clin Chem, 2003, 49(6): 853-860.
13. Afonina, I. A., et al, Biotechniques, 2002, 32: 940-944, 946-949.
14. Lukhtanov, E. A., et al, Nucleic Acids Res, 2007, 35: e30.
15.

What is claimed is:

1. A method for detecting the presence of a variation or the type of a variation in a target nucleic acid, comprising:
    (1) amplifying a fragment comprising the nucleic acid to be tested using asymmetric PCR after adding a probe to the amplification reaction mixture for the asymmetric PCR, wherein one PCR amplification primer in the reaction mixture is relatively in excess and the strand produced with the elongation of said primer hybridizes with the probe and the polymerase used in the asymmetric PCR has an exonuclease activity; wherein the probe is a self-quenched nucleic acid probe, wherein the probe is labeled at opposite ends with a fluorescent group and a quenching group in such a way that fluorescence or fluorescence intensity increases when the probe hybridizes with the target nucleic acid sequence compared to fluorescence or fluorescence intensity in the absence of the target nucleic acid sequence, wherein: if the 5' end of the probe is labeled with the fluorescent group, then the 3' end of the probe is labeled with the quenching group; or if the 3' end of the probe is labeled with the fluorescent group, then the 5' end is labeled with the quenching group, and said probe does not comprise a modification that is able to resist the exonuclease activity of a polymerase; and wherein the probe is a hairpin structure probe; and
    (2) determining whether the target nucleic acid has a sequence variation compared to a reference or wild-type nucleic acid by melting curve analysis of the amplification product.

2. The method of claim 1, wherein the amplification reaction further comprises a reference nucleic acid or wild-type nucleic acid.

3. The method of claim 1, wherein said variation is a mononucleotide variation.

4. The method of claim 3, wherein the single nucleotide mutation may be conversion, transversion, insertion or deletion of a single base at one or more of the same or different positions in the nucleic acid sequence of the same gene locus among different individuals of the same species.

5. The method of claim 1, wherein the length of the probe is 5-100, 10-100, 10-50, 15-50, 20-50, 10-40, 10-20, 20-30, 30-40, 15-30, 20-40, or 15-25 bases.

6. The method of claim 1, wherein the probe comprises a nucleic acid sequence fully complementary to the target nucleic acid sequence.

7. The method of claim 1, wherein the probe comprises a mismatch with respect to the target nucleic acid sequence.

8. The method of claim 7, wherein the probe comprises 1-10, 1-5, 1-4, 1-3, 1-2, 1, or 2 mismatches.

9. The method of claim 7, wherein the mismatch is a conversion, transversion, insertion, or deletion of a single base.

10. The method of claim 1, wherein the probe comprises no modification, in addition to the labeling of said fluorescent group and said quenching group.

11. The method of claim 1, wherein the probe comprises bases that are able to increase or decrease the binding ability of the probe.

12. The method of claim 11, wherein the bases that are able to increase the binding ability of the probe include locked nucleic acid.

13. The method of claim 11, wherein the bases that are able to decrease the binding ability of the probe include a universal binding base I.

14. A method for detecting the presence of a nucleic acid variation or for detecting the exact type of variation, comprising:
    (1) contacting a plurality of target nucleic acid segments of a genome with a plurality of probes, wherein the probe is a self-quenched nucleic acid probe, wherein the probe is labeled at opposite ends with a fluorescent group and a quenching group in such a way that fluorescence or fluorescence intensity increases when the probe hybridizes with the target nucleic acid sequence compared to fluorescence or fluorescence intensity in the absence of the target nucleic acid sequence, wherein: if the 5' end of the probe is labeled with the fluorescent group, then the 3' end of the probe is labeled with the quenching group; or if the 3' end of the probe is labeled with the fluorescent group, then the 5' end is labeled with the quenching group, and said probe does not comprise a modification that is able to resist the exonuclease activity of a polymerase; and wherein the probe is a hairpin structure probe;
    (2) amplifying the target nucleic acid segments using asymmetric PCR, wherein one PCR amplification primer in the reaction mixture for the asymmetric PCR is relatively in excess and the strand produced with the elongation of said primer hybridizes with the probe, and the polymerase used in the asymmetric PCR has an exonuclease activity;
    (3) monitoring any changes of fluorescence resulting from interactions between the probes and the amplified target nucleic acid segments in response to a gradual increase or decrease in the temperature of said reaction mixture at a time following the asymmetric PCR amplification step, thereby simultaneously obtaining melting curves corresponding to each of the probes;
    (4) making derivation for the melting curve obtained in step (3), and taking the negative derivative thereof (−dF/dT), thereby obtaining the melting temperature corresponding to each of the probes; and
    (5) comparing the melting temperatures obtained in step (4) corresponding to each of the nucleic acid sequences to be tested and each of the probes, to analyze whether each of the nucleic acid sequences to be tested has a target sequence variation.

15. The method of claim 14, wherein the amplification reaction further comprises a reference nucleic acid or wild-type nucleic acid.

16. The method of claim 14, wherein said variation is a mononucleotide variation.

17. The method of claim 16, wherein the single nucleotide mutation may be conversion, transversion, insertion or deletion of a single base at one or more of the same or different positions in the nucleic acid sequence of the same gene locus among different individuals of the same species.

18. The method of claim 14, wherein the length of the probe is 5-100, 10-100, 10-50, 15-50, 20-50, 10-40, 10-20, 20-30, 30-40, 15-30, 20-40, or 15-25 bases.

19. The method of claim 14, wherein the probe comprises a nucleic acid sequence fully complementary to the target nucleic acid sequence.

20. The method of claim 14, wherein the probe comprises a mismatch with respect to the target nucleic acid sequence.

21. The method of claim 20, wherein the probe comprises 1-10, 1-5, 1-4, 1-3, 1-2, 1, or 2 mismatches.

22. The method of claim 20, wherein the mismatch is a conversion, transversion, insertion, or deletion of a single base.

23. The method of claim 14, wherein the probe comprises no modification, in addition to the labeling of said fluorescent group and said quenching group.

24. The method of claim 14, wherein the probe comprises bases that are able to increase or decrease the binding ability of the probe.

25. The method of claim 24, wherein the bases that are able to increase the binding ability of the probe include locked nucleic acid.

26. The method of claim 24, wherein the bases that are able to decrease the binding ability of the probe include a universal binding base I.

27. A method for detecting target sequence variation or the type of variation by nucleic acid amplification melting curve analysis using self-quenched probes, wherein the sequences of the self-quenched probes used in the method comprise or are the fully complementary sequences of the wild-type or variant target nucleic acid sequences; or sequences having several mismatches when compared with the fully complementary sequence of the wild-type or variant target nucleic acid sequences, the self-quenched probe is labeled with a fluorescent group and a quenching group, so that, when compared with the situation where a target nucleic acid sequence is absent, fluorescence or fluorescence intensity increases when the probe hybridizes with the target nucleic acid sequence, and said probe does not comprise a modification that is able to resist the exonuclease activity of a polymerase, and wherein the probe is a hairpin structure probe; and wherein the method comprises the steps of:

(1) preparing an amplification reaction solution for asymmetric PCR, and pre-adding in the amplification reaction solution self-quenched probes, wherein one PCR amplification primer in the amplification reaction solution is relatively in excess and the strand produced with the elongation of said primer hybridizes with the probes, and the polymerase used in the amplification reaction solution has an exonuclease activity;

(2) carrying out amplification using asymmetric PCR;

(3) performing melting curve analysis; and (4) analyzing whether a variation exists or determining a type of variation, based on the melting temperature of the hybrid formed between the self-quenched probe and the target nucleic acid.

* * * * *